United States Patent
Coles et al.

(10) Patent No.: US 10,598,670 B2
(45) Date of Patent: Mar. 24, 2020

(54) METHODS AND COMPOSITIONS FOR DIAGNOSIS AND TREATMENT OF AUTOIMMUNE DISEASE SECONDARY TO MULTIPLE SCLEROSIS

(71) Applicant: Cambridge Enterprise Limited, Cambridge (GB)

(72) Inventors: Alasdair J. Coles, Cambridge (GB); Joanne L. Jones, Cambridge (GB); Alastair Compston, Cambridge (GB)

(73) Assignee: Cambridge Enterprise Limited, Cambridge (GB)

(*) Notice: Subject to any disclaimer, the term of this patent is extended or adjusted under 35 U.S.C. 154(b) by 287 days.

(21) Appl. No.: 15/013,808

(22) Filed: Feb. 2, 2016

(65) Prior Publication Data

US 2016/0356788 A1  Dec. 8, 2016

Related U.S. Application Data

(62) Division of application No. 13/123,188, filed as application No. PCT/IB2009/007327 on Oct. 8, 2009, now abandoned.

(60) Provisional application No. 61/198,631, filed on Nov. 7, 2008, provisional application No. 61/197,187, filed on Oct. 24, 2008, provisional application No. 61/195,658, filed on Oct. 8, 2008.

(51) Int. Cl.
*G01N 33/68* (2006.01)
*C12Q 1/6883* (2018.01)

(52) U.S. Cl.
CPC ....... *G01N 33/6869* (2013.01); *C12Q 1/6883* (2013.01); *C12Q 2600/106* (2013.01); *C12Q 2600/156* (2013.01); *C12Q 2600/158* (2013.01); *C12Q 2600/172* (2013.01); *G01N 2800/285* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,045,501 | A | 4/2000 | Elsayed et al. |
| 6,351,720 | B1 | 2/2002 | Hoshina et al. |
| 6,561,976 | B2 | 5/2003 | Elsayed et al. |
| 6,561,977 | B2 | 5/2003 | Williams et al. |
| 6,755,784 | B2 | 6/2004 | Williams et al. |
| 6,869,399 | B2 | 3/2005 | Williams et al. |
| 6,908,432 | B2 | 6/2005 | Elsayed et al. |
| 7,141,018 | B2 | 11/2006 | Williams et al. |
| 7,410,780 | B2 | 8/2008 | Presnell et al. |
| 2005/0095223 | A1 | 5/2005 | Sivakumar et al. |
| 2007/0048272 | A1 | 3/2007 | Nelson et al. |
| 2007/0122413 | A1 | 5/2007 | Sivakumar et al. |
| 2008/0241098 | A1 | 10/2008 | Young et al. |

FOREIGN PATENT DOCUMENTS

| | | |
|---|---|---|
| WO | 03/020759 | 3/2003 |
| WO | 2003/050257 | 6/2003 |
| WO | 04/084835 | 10/2004 |
| WO | 05/030196 | 4/2005 |

OTHER PUBLICATIONS

Vogelzang, A. and King, C. Frontiers Bioscience 2008:5304-5315.*
Murray, "Diagnosis and treatment of multiple sclerosis," BMJ 332:525-527 (2006).
Nurieva et al., "Essential autocrine regulation by IL-21 in the generation of inflammatory T cells," Nature 448:480-483 (2007).
Polman et al., "Drug treatment of multiple sclerosis," BMJ 321:490-494 (2000).
Powrie et al. "Phenotypically distinct subsets of CD4+ T cells induce or protect from chronic intestinal inflammation in C. B-17 scid mice," Int. Immunol. 5:1461-1471 (1993).
Ramagopalan et al., "Genomewide study of multiple sclerosis," N. Engl. J. Med. 357:2199-2200 (2007).
Reiff, "A review of Campath in autoimmune disease: biologic therapy in the gray zone between immunosuppression and immunoablation," Hematology 10:79-93 (2005).
Rose et al., "Monoclonal antibody treatments for multiple sclerosis," Cuff Neurol Neurosci Rep 8:419-426 (2008).
Sakaguchi et al., "Immunologic self-tolerance maintained by activated T cells expressing IL-2 receptor alpha-chains (CD25). Breakdown of a single mechanism of self-tolerance causes various autoimmune diseases," J. Immunol. 155:1151-1164 (1995).
Simpson et al., "Rationale for cytotoxic monoclonal antibodies in MS," Int. MS. J. 14:48-56 (2007).
Sivakumar et al., "Interleukin-21 is a T-helper cytokine that regulates humoral immunity and cell-mediated anti-tumour responses," Immunology 112:177-182 (2004).
Sonderegger et al., "IL-21 and IL-21 R are not required for development of Th17 cells and autoimmunity in vivo," Eur. J. Immunol. 38:1833-1838 (2008).
Spolski et al., "Interleukin-21: basic biology and implications for cancer and autoimmunity," Annu. Rev. Immunol. 26:57-79 (2008).
Spolski et al., "The Yin and Yang of interleukin-21 in allergy, autoimmunity and cancer," Curro Opin. Immunol. 20:295-301 (2008).
Thompson et al., "B-cell reconstitution and BAFF after alemtuzumab (Campath-1H) treatment of multiple sclerosis," J Clin Immunol. 30:99-105 (2010).

(Continued)

*Primary Examiner* — G. R. Ewoldt
(74) *Attorney, Agent, or Firm* — Steptoe & Johnson LLP; Z. Ying Li; Wyan-Ching M. Lee

(57) ABSTRACT

The invention provides methods of diagnosing and treating multiple sclerosis (MS) patients, including methods of identifying and treating multiple sclerosis patients who are at increased risk of developing a secondary autoimmune disease following lymphocyte depletion, caused, e.g., by treatment with an anti-CD52 antibody. Also embraced are methods of selecting treatment regimens for MS patients, and reagents useful in the above methods.

11 Claims, 12 Drawing Sheets

Specification includes a Sequence Listing.

(56) References Cited

OTHER PUBLICATIONS

Ting et al., "Acquired autoimmune thrombocytopenia post-bone marrow transplantation for severe combined immunodeficiency," Bone Marrow Transplant. 21:841-843 (1998).
Van Heel et al., "A genome-wide association study for celiac disease identifies risk variants in the region harboring IL2 and IL21," Nat. Genet. 39:827-829 (2007).
Vendrame et al., "Defective lymphocyte caspase-3 expression in type 1 diabetes mellitus," Eur. J. Endocrinol. 152:119-125 (2005).
Vendrame et al., "Impaired caspase-3 expression by peripheral T cells in chronic autoimmune thyroiditis and in autoimmune polyendocrine syndrome-2," J. Clin. Endocrinol. Metab. 91:5064-5068 (2006).
Vollmer et al., "Differential effects of IL-21 during initiation and progression of autoimmunity against neuroantigen," J. Immunol. 174:2696-2701 (2005).
Waldmann and Hale, "CAMPATH: from concept to clinic," Philos. Trans. R. Soc. Lond. B. Biol. Sci. 360:1707-1711 (2005).
Waldmann, "The History of Alemtuzumab (CAMPATH-1H) Antibody," Chronic Lymphocytic Leukemia, The Cutting Edge 6:1-5 (2001).
Weiss et al., "Immunotherapy of cancer by IL-12-based cytokine combinations," Expert Opin. Biol. Ther. 7:1705-1721 (2007).
Wu et al., "Homeostatic proliferation is a barrier to transplantation tolerance," Nat. Med. 10:87-92 (2004).
Yeo et al., "A second major histocompatibility complex susceptibility locus for multiple sclerosis," Ann. Neurol. 61:228-236 (2007).
Zandman-Goddard et al., "HIV and autoimmunity," Autoimmun. Rev. 1:329-337 (2002).
Zeng et al., "Measurement of interleukin-21," Curro Protoc. Immunol. 6:6.30.1-6.30.8 (2007).
Zhang et al., "Lymphopenia and interleukin-2 therapy alter homeostasis of CD4+CD25+ regulatory T cells," Nat. Med. 11:1238-1243 (2005).
Azzopardi et al., "Predicting autoimmunity after alemtuzumab treatment of multiple sclerosis" J. Neurol Neurosurg Psychiatry 2014; 85:795-798, doi:10.1136/jnnp-2013-307042.
Alderuccio et al., "An autoimmune disease with multiple molecular targets abrogated by the transgenic expression of a single autoantigen in the thymus," J. Exp. Med., 178:419-426 (1993).
Awasthi et al., "Interplay between effector Th17 and regulatory T cells," J. Clin. Immunol. 28:660-670 (2008).
Bloom et al., "CD4+ CD25+ FOXP3+ regulatory T cells increase de novo in kidney transplant patients after immunodepletion with Campath-1H," Am. J. Transplan. 8:793-802 (2008).
Capello et al., "Marburg type and Bala's concentric sclerosis: rare and acute variants of multiple sclerosis," Neurol. Sci., 25 Suppl., 4:S361-S363 (2004).
Chaudhuri, "Lessons for clinical trials from natalizumab in multiple sclerosis," BMJ 332:416-419 (2006).
Chen et al., "Characteristics of autoimmune thyroid disease occurring as a late complication of immune reconstitution in patients with advanced human immunodeficiency virus (HIV) disease," Medicine (Baltimore) 84:98-106 (2005).
Cho et al., "Homeostasis-stimulated proliferation drives naive T cells to differentiate directly into memory T cells," J. Exp. Med. 192:549-556 (2000).
Coles et al., "Alemtuzumab versus interferon beta-1a in early relapsing-remitting multiple sclerosis: post-hoc and subset analyses of clinical efficacy outcomes," Lancet Neurol. 10:338-348 (2011).
Coles et al., "Alemtuzumab vs. interferon beta-1a in early multiple sclerosis," N. Engl. J. Med. 359:1786-1801 (2008).
Coles et al., "Monoclonal antibody treatment exposes three mechanisms underlying the clinical course of multiple sclerosis," Ann. Neurol. 46:296-304 (1999).
Coles et al., "Pulsed monoclonal antibody treatment and autoimmune thyroid disease in multiple sclerosis," Lancet 354:1691-1695 (1999).
Coles et al., "The window of therapeutic opportunity in multiple sclerosis: evidence from monoclonal antibody therapy," J. Neurology 253:98-108 (2006).
Compston et al., "Multiple sclerosis," Lancet 372:1502-1517 (2008).
Compston, "Revisiting the pathogenesis of multiple sclerosis revisited," Int. MS. J. 10:29-31 (2003).
Cox et al., "Lymphocyte homeostasis following therapeutic lymphocyte depletion in multiple sclerosis," Eur. J. Immunol. 35:3332-3342 (2005).
Cree et al., "Emerging monoclonal antibody therapies for multiple sclerosis," Neurologist 12:171-178 (2006).
Crowe et al., "Humanized monoclonal antibody CAMPATH-1 H: myeloma cell expression of genomic constructs, nucleotide sequence of cDNA constructs and comparison of effector mechanisms of myeloma and Chinese hamster ovary cell-derived material," Clin. Exp. Immunol. 87:105-110 (1992).
Daikeler et al., "Autoimmunity following haematopoietic stem-cell transplantation," Best. Pract. Res. Clin. Haematol. 20:349-360 (2007).
Davis et al., "Interleukin-21 signaling: functions in cancer and autoimmunity," Clin. Cancer Res. 13:6926-6932 (2007).
De Kleer et al., "Autologous stem cell transplantation for autoimmunity induces immunologic self-tolerance by reprogramming autoreactive T cells and restoring the CD4+CD25+ immune regulatory network," Blood 107:1696-1702 (2006).
Distler et al., "Expression of Interleukin-21 receptor in epidermis from patients with systemic sclerosis," Arthritis & Rheumatism 52:856-864 (2005).
Ettinger et al., "The role of IL-21 in regulating B-cell function in health and disease," Immunol. Rev. 223:60-86 (2008).
Ge et al., "Competition for self-peptide-MHC complexes and cytokines between naive and memory CD8+ T cells expressing the same or different T cell receptors," Proc. Natl. Acad. Sci. 101:3041-3046 (2004).
Ge et al., "Dependence of lymphopenia-induced T cell proliferation on the abundance of peptide/MHC epitopes and strength of their interaction with T cell receptors," Proc. Natl. Acad. Sci. 98:1728-1733 (2001).
Gilleece et al., "Effect of Campath-1H antibody on human hematopoietic progenitors in vitro," Blood 82:807-812 (1993).
Glas et al., "Novel genetic risk markers for ulcerative colitis in the IL2/IL21 region are in epistasis with IL23R and suggest a common genetic background for ulcerative colitis and celiac disease," Am. J. Gastroenterol. 104:1737-1744 (2009).
Goldrath et al., "Naive T cells transiently acquire a memory-like phenotype during homeostasis-driven proliferation," J. Exp. Med. 92:557-564 (2000).
Hainfellner et al., "Devic's neuromyelitis optica and Schilder's myelinoclastic diffuse sclerosis," J. Neurol. Neurosurg. Psychiatr. 55:1194-1196 (1992).
Hakim et al., "Reconstitution of the lymphocyte compartment after lymphocyte depletion: a key issue in clinical immunology," Eur. J. Immunol. 35:3099-3102 (2005).
Holmdahl, "IL-21 and autoimmune disease—hypothesis and reality?" Eur. J. Immunol. 38:1800-1802 (2008).
International Multiple Sclerosis Genetics Consortium (IMSGC), Lancet Neurol. 7:567-569 (2008).
Jones et al., "IL-21 drives secondary autoimmunity in patients with multiple sclerosis, following therapeutic lymphocyte lepletion with alemtuzumab (Campath-1H)," J. Clin. Invest. 119:2052-2061 (2009).
Jones et al., "Improvement in disability after alemtuzumab treatment of multiple sclerosis is associated with neuroprotective autoimmunity," Brain 133:2232-47 (2010).
Jubault et al., "Sequential occurrence of thyroid autoantibodies and Graves' disease after immune restoration in severely immunocompromised human immunodeficiency virus-1-infected patients," J. Clin. Endocrinol. Metab. 85:4254-4257 (2000).
Kassiotis et al., "Involvement of avidity for major histocompatibility complex in homeostasis of naive and memory T cells," J. Exp. Med. 197:1007-1016 (2003).
Katsara et al., "Towards immunotherapeutic drugs and vaccines against multiple sclerosis," Acta. Biochim. Biophys. Sin. (Shanghai) 40:636-642 (2008).

(56) References Cited

OTHER PUBLICATIONS

Khoruts et al., "A causal link between lymphopenia and autoimmunity," Immunol. Lett. 98:23-31 (2004).

King et al., "Homeostatic expansion of T cells during immune insufficiency generates autoimmunity," Cell 117:265-277 (2004).

Kom et al., "IL-21 initiates an alternative pathway to induce proinflammatory T H17 cells," Nature 448:484-488 (2007).

Krupica et al., "Autoimmunity during lymphopenia: a two-hit model," Clin. Immunol. 120: 121-128 (2006).

Linker and Kieseier, "Innovative monoclonal antibody therapies in multiple sclerosis," Therapeutic Advances in Neurological Disorders 1(1):33-42 (2008).

Lublin et al., "Defining the clinical course of multiple sclerosis: results of an international survey. National Multiple Sclerosis Society (USA) Advisory Committee on Clinical Trials of New Agents in Multiple Sclerosis," Neurology 46:907-911 (1996).

Lutterotti et al., "Getting specific: monoclonal antibodies in multiple sclerosis," Lancet Neurol. 7:538-547 (2008).

Marleau et al., "T cell homeostasis in tolerance and immunity," J. Leukocyte Biol. 78:575-584 (2005).

McFarland and Martin, "Multiple sclerosis: a complicated picture of autoimmunity," Nature Immunology 8:913-919 (2007).

McHugh et al., "Cutting edge: depletion of CD4+CD25+ regulatory T cells is necessary, but not sufficient, for induction of organ-specific autoimmune disease," J. Immunol. 168:5979-5983 (2002).

Miller et al., "Primary-progressive multiple sclerosis," Lancet Neurol. 6:903-912 (2007).

Murali-Krishna et al., "Cutting edge: naive T cells masquerading as memory cells," J. Immunol. 165:1733-1737 (2000).

Buttmann et al., "Treating multiple sclerosis with monoclonal antibodies," Expert Rev Neurother 8(3):433-55 (2008).

\* cited by examiner

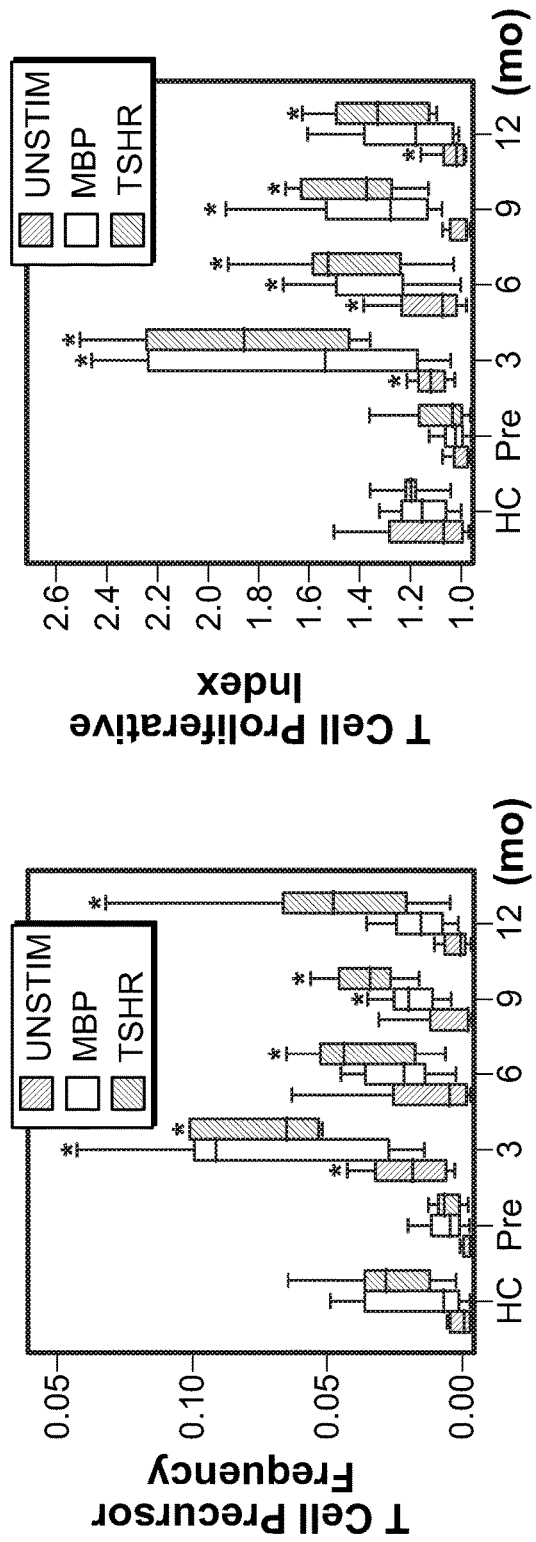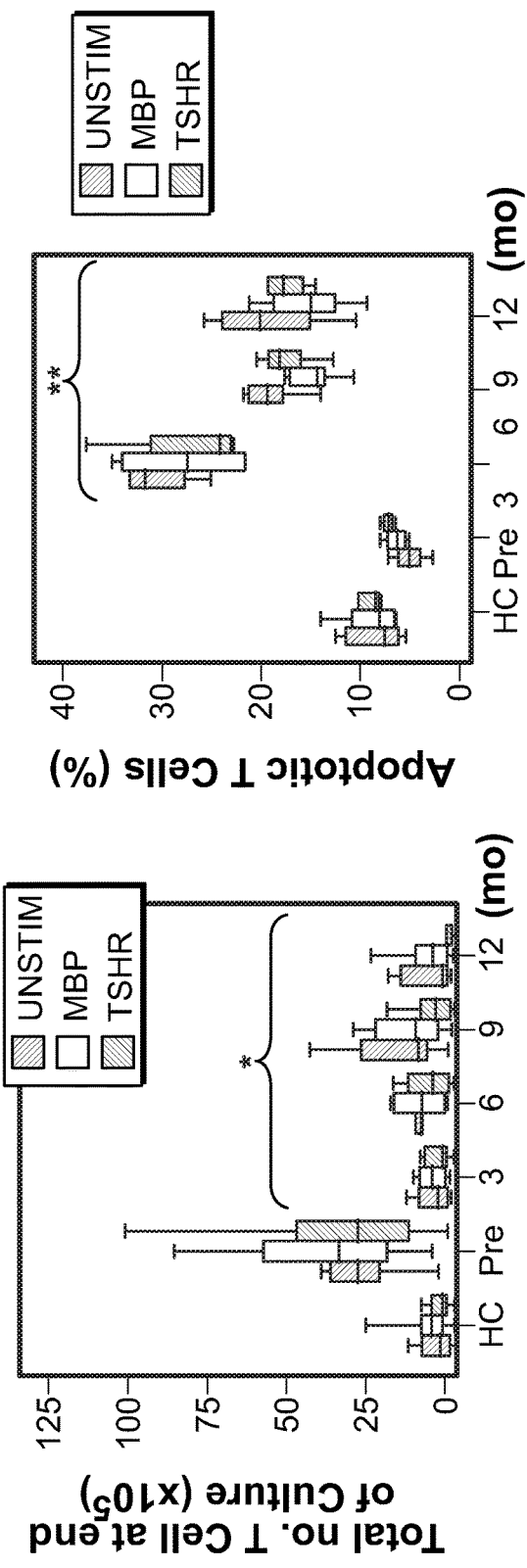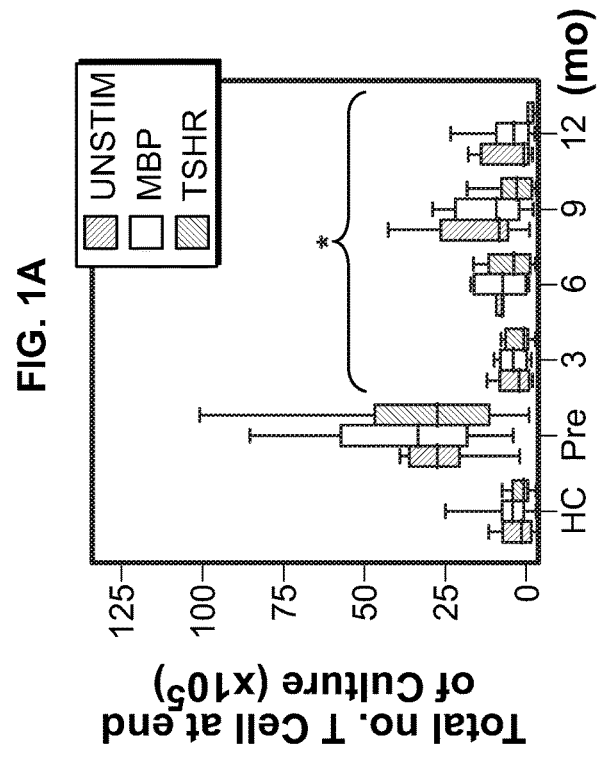

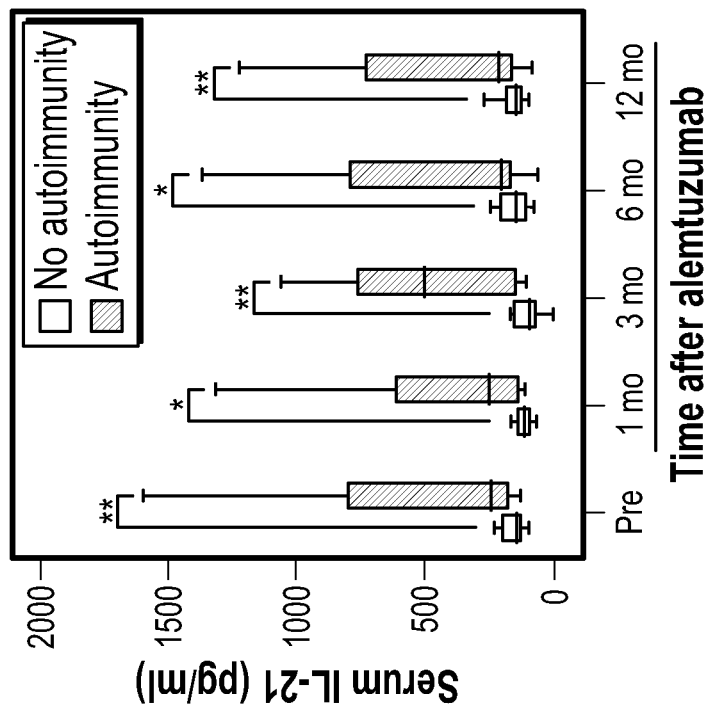
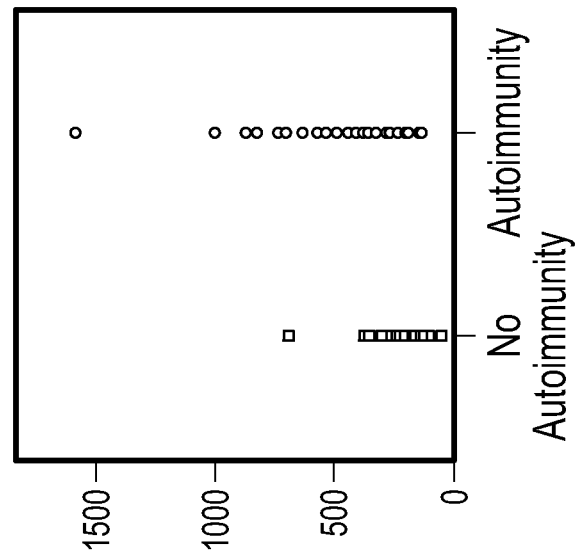
FIG. 6A
FIG. 6B

SEQUENCE LISTING

<160> NUMBER OF SEQ ID NOS: 39

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cctgtggatg actgagtacc tgaa                                          24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cacctaccca gcctccgtta                                               20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cggcacctgc acacctggat c                                             21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttcagtcgga aatgaccaga ca                                            22

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaggatgtgg tggagcagag a                                             21

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tgaccatcca ctctaccctc ccaccc                                        26

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaaagcattt tgagcaggag agtatt                                        26

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggccattaag atgagcacca a                                             21

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
ctagagctct gccacctctc catt                                          24

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aagaaagtgg cccatttaac ag                                            22

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agaaagcagg acaattccat aggt                                          24

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
caactcaagg tccatgcctc tgg                                           23

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ctgcctggca gcccttt                                                    17

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
ctccaagaag ggccagttct t                                               21

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 15
tcaaggacca ccgcatctct acatt                                           25

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gtggagaccc acctgctc                                                   18

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ggacacatca gatttatcca aatcc                                           25

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 18
ctgccatcag cactctatag tccgaaacaa                                      30

```
<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aggaggagat ggaaagggaa ctt                                          23

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acctcaattc tgatctgctc acttct                                       26

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
ctccctacag ggtcatgctc tatcagattt cag                               33

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aagatcatac atggaagcga atca                                         24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgagatgtca ttccagtgct ttta                                         24

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
ctggaatatc cctggacaac agttataaa                                    29

<210> SEQ ID NO 25
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgcgaactaa caggcaagca                                                   20

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gaacctctgg tttgcgaatc tc                                                22

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
caaagttgtc gaagccaacc ctagaaaacc tta                                    33

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cagtgacctt cgctccacat c                                                 21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acggatcctc tttttgcata g                                                 21

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
actccacccg ttcccactgc cc                                                22

<210> SEQ ID NO 31
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tttctgacgg caacttcaac t                                              21

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggtgcacagg gccttgag                                                  18

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
tgtcgccctt ttctactttg ccagca                                         26

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gctgtatagc tgcttccagt gtag                                           24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gctatcttcc agcctgtctt ctct                                           24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
agccctggca tgtcaacagc gttc                                           24

<210> SEQ ID NO 37
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
accacaagga tttctcatga tacc                                              24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccatatgaca aaatgctcaa ggaa                                              24

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
tagccacagc cacctctctc cct                                               23
```

METHODS AND COMPOSITIONS FOR DIAGNOSIS AND TREATMENT OF AUTOIMMUNE DISEASE SECONDARY TO MULTIPLE SCLEROSIS

This application is a divisional application of U.S. patent application Ser. No. 13/123,188, filed Jun. 7, 2011 (now abandoned), which is a national stage application under 35 U.S.C. § 371 of International Application PCT/IB2009/007327, filed Oct. 8, 2009, which application claims priority to U.S. Provisional Application 61/195,658, filed Oct. 8, 2008, U.S. Provisional Application 61/197,187, filed Oct. 24, 2008, and U.S. Provisional Application 61/198,631, filed Nov. 7, 2008. The contents of the foregoing applications are hereby incorporated by reference in their entirety.

The Sequence Listing associated with this application is being submitted electronically via EFS-WEB in text format, and is hereby incorporated by reference into the specification. The name of the text file containing the Sequence Listing is 001662_0019_302 Sequence_Listing.txt. The text file is 9,001 bytes in size, and was created on Feb. 1, 2016.

BACKGROUND OF THE INVENTION

Multiple sclerosis ("MS") is an inflammatory autoimmune disorder of the central nervous system (Compston and Coles, *Lancet* 372, 1502-17 (2008)). With a prevalence of about one in 1000, MS is the most common cause of neurological disability in young adults (Polman and Uitdehaag, *BMJ* 321, 490-4 (2000)). MS involves engagement of the immune system, acute inflammatory injury of axons and glia, recovery of function and structural repair, post-inflammatory gliosis, and neurodegeneration (see, e.g., Compston and Coles, 2008). These sequential processes underlie a clinical course characterized by episodes with recovery, episodes leaving persistent deficits, and secondary progression. Id.

The goal of MS treatment is to reduce the frequency and severity of relapses, prevent disability arising from disease progression, and promote tissue repair (Compston and Coles, 2008). The primary approach to MS treatment is modulation or suppression of the immune system. Currently available MS drugs include interferon beta-1a (e.g., AVONEX and REBIF), interferon beta-1b (e.g., BETASERON), glatiramer acetate (e.g., COPAXONE), mitoxantrone (e.g., NOVANTRONE), and natalizumab (e.g., TYSABRI). Another promising new drug for MS is alemtuzumab (CAMPATH-1H).

Alemtuzumab is a humanized monoclonal antibody directed against CD52, a protein widely distributed on the surface of lymphocytes and monocytes but with unknown function. Alemtuzumab has been used to treat B-cell chronic lymphocytic leukaemia. A single pulse of treatment leads to a rapid, profound, and prolonged lymphopenia. Cell numbers recover but at varying rates; CD4+ T cells are particularly slow to recover, remaining depleted for at least five years (Coles et al., *Journal of Neurology* 253, 98-108 (2006)). A phase 2 trial (CAMMS-223 study group; Coles et al., *N. Engl. J. Med.* 359, 1786-1801 (2008)) has shown that alemtuzumab is highly effective in treating early relapsing-remitting multiple sclerosis. This drug reduces the risk of disease activity and accumulation of disability by over 70% compared to interferon-beta in patients with early relapsing-remitting multiple sclerosis. The principal adverse effect is autoimmunity, arising in the setting of T cell lymphopenia months to years after dosing. About 20%-30% of patients develop thyroid autoimmunity, mainly Graves' disease (Coles et al., *Lancet* 354, 1691-1695 (1999)), and 3% have immune thrombocytopenia (ITP) (Coles et al., 2008). Single cases of Goodpasture's disease, autoimmune neutropenia (Coles et al., *Journal of Neurology* 253, 98-108 (2006)), and autoimmune haemolytic anaemia (unpublished observation) also have been observed. In addition, a further 5.5% of patients develop sustained non-thyroid autoantibodies without clinical disease (Coles et al., 2006). The timing and spectrum of autoimmunity after alemtuzumab is similar to that seen in other examples of "reconstitution autoimmunity" in other clinical contexts; for example, autoimmune thyroid disease and autoimmune cytopenias also predominate months to years after hematopoietic stem cell transplantation or antiretroviral treatment of HIV (Chen et al., *Medicine (Baltimore)* 84, 98-106 (2005); Daikeler and Tyndall, *Best. Pract. Res. Clin. Haematol.* 20, 349-360 (2007); Jubault et al., *J. Clin. Endocrinol. Metab.* 85, 4254-4257 (2000); Ting, Ziegler, and Vowels, *Bone Marrow Transplant.* 21, 841-843 (1998); Zandman-Goddard and Shoenfeld, *Autoimmun. Rev.* 1, 329-337 (2002)).

While autoimmunity arising in the context of lymphopenia is well recognized in animal models, it is rarely encountered and, hence, difficult to study in humans. Most lymphopenic subjects do not develop autoimmunity, suggesting that additional factors are involved (Krupica et al., *Clin Immunol* 120, 121-128 (2006)). It remains unclear what those additional factors are. Depletion of T regulatory cells has been considered as one factor, as seen in the murine colitis and gastritis models (Alderuccio et al., *J Exp. Med* 178, 419-426 (1993); McHugh et al., *J. Immunol* 168, 5979-5983 (2002); Powrie et al., *Int. Immunol* 5, 1461-1471 (1993); Sakaguchi et al., *J Immunol* 155, 1151-1164 (1995)). However, it has been observed that T regulatory cells are increased after alemtuzumab in human patients and thereafter return to normal levels (Cox et al., *Eur J Immunol* 35, 3332-3342 (2005)). This observation has since been replicated (Bloom et al., *Am J Transplant.* 8, 793-802 (2008)) and is in keeping with other experimental lymphopenic models (de Kleer, I. et al., *Blood* 107, 1696-1702 (2006); Zhang, H. et al., *Nat Med* 11, 1238-1243 (2005)).

SUMMARY OF THE INVENTION

We have invented new and useful methods and compositions for improving risk management in MS treatment. The methods and compositions reduce MS treatment side effects such as secondary autoimmunity, and help health care providers and patients in selecting regimens for MS treatment and post-treatment monitoring. The methods and compositions of this invention are based on our discovery that in multiple sclerosis (MS) patients, elevated IL-21, detectable even before lymphocyte depleting therapy such as alemtuzumab therapy, correlates with increased risk of developing secondary autoimmunity after the therapy. We have further discovered that an individual's IL-21 level may be genetically determined: single nucleotide polymorphisms (SNP) genotypes of A/A at SNP rs13151961, G/G at SNP rs6822844, and C/C at SNP rs6840978 are associated with elevated IL-21.

Accordingly, the present invention provides methods for identifying an MS patient who has elevated interleukin-21 (IL-21) compared to IL-21 in a subject without an autoimmune disease. In some embodiments, the methods comprise the step of measuring IL-21 in a blood sample from the MS patient, thereby identifying an MS patient having elevated IL-21 compared to said subject. Alternatively, the methods comprise the step of genotyping the patient to detect the presence or absence in the patient of one or more genotypes of single nucleotide polymorphisms (SNPs) associated with elevated IL-21 such as those selected from the group consisting of: A/A at SNP rs13151961, G/G at SNP rs6822844, and C/C at SNP rs6840978, wherein the presence of one or more of said genotypes is associated with elevated IL-21.

The invention further provides methods for identifying an MS patient who is at increased risk of developing a secondary autoimmune disease following lymphocyte depletion. In some embodiments, the methods comprise the step of ascertaining (e.g., by measuring) the level of interleukin-21 (IL-21) in a blood sample from the MS patient, wherein an elevated IL-21 level compared to a subject without an autoimmune disease indicates that the patient is at increased risk of developing a secondary autoimmune disease compared to MS patients without elevated IL-21. Alternatively, the methods comprise the step of ascertaining (e.g., by genotyping) the presence or absence in the patient of one or more genotypes of single nucleotide polymorphisms (SNPs) associated with elevated IL-21 such as those selected from the group consisting of: A/A at SNP rs13151961, G/G at SNP rs6822844, and C/C at SNP rs6840978, wherein the presence of one or more (e.g., two or three) of said genotypes is associated with an increased risk of developing a secondary autoimmune disease compared to MS patients without said one or more genotypes. These methods optionally comprise the step of informing the patient and/or his/her health care provider of said increased risk, and/or the step of recording the increased risk.

The invention further provides methods for selecting or identifying an MS patient in need of heightened monitoring for development of a secondary autoimmune disease after lymphocyte depleting therapy. These methods may comprise the step of measuring IL-21 in a blood sample from the MS patient, wherein elevated IL-21 in said patient compared to a subject without an autoimmune disease indicates that the patient is in need of heightened monitoring for development of a secondary autoimmune disease compared to MS patients without elevated IL-21. Alternatively, the methods may comprise the step of genotyping the patient to detect the presence or absence of one or more genotypes of SNPs associated with elevated IL-21 such as those selected from the group consisting of: A/A at SNP rs13151961, G/G at SNP rs6822844, and C/C at SNP rs6840978, wherein the presence of one or more of said SNPs indicates that the patient is in need of heightened monitoring for development of a secondary autoimmune disease compared to MS patients without said one or more genotypes. These methods optionally comprise the step of informing the patient and/or his/her health care provider of the need for heightened monitoring, and/or the step of recording the need.

The invention also provides methods for informing a treatment for an MS patient, comprising measuring IL-21 in a blood sample from said patient or genotyping the patient for the presence or absence of the aforementioned three SNP phenotypes, and selecting a treatment regimen appropriate for the IL-21 measurement or genotype.

The invention provides methods for treating MS in a patient known to be in need thereof, comprising the steps of (a) obtaining or ascertaining information on (i) IL-21 in a blood sample from the patient (e.g., by measuring IL-21 in the sample); or (ii) the presence or absence of one or more genotypes of single-nucleotide polymorphisms (SNPs) associated with elevated IL-21 such as those selected from the group consisting of: A/A at SNP rs13151961, G/G at SNP rs6822844 G/G, and C/C at SNP rs6840978 (e.g., by genotyping the patient); (b) administering a therapeutic agent for multiple sclerosis to said patient, and (c) optionally monitoring the patient for development of a secondary autoimmune disease. In some embodiments, the methods of treatment are used on patients who are found to have normal IL-21 levels and/or do not have any one of the aforementioned three IL-21 SNP genotypes. Also embraced by the invention are anti-CD52 antibodies (e.g., alemtuzumab or a biologically similar agent), or antigen-binding portions thereof, that are used in these treatment methods, and uses of these antibodies or antigen-binding portions in the manufacture of a medicament for use in these treatment methods. Further embraced by the invention are therapeutic regimens using these methods of treatment.

The invention provides methods for reducing the occurrence or severity of a secondary autoimmune disease in a multiple sclerosis patient who has been or will be treated with a lymphocyte depleting therapy, wherein the secondary autoimmune disease occurs after treatment with the lymphocyte depleting therapy, comprising the step of administering an IL-21 antagonist, e.g., prior to, during, or subsequent to the treatment with the lymphocyte depleting therapy. Also embraced by the invention are IL-21 antagonists for use in these methods (e.g., an anti-IL-21 or anti-IL-21 receptor antibody, or an antigen-binding portion thereof; or a soluble IL-21 receptor), and uses of these IL-21 antagonists in the manufacture of a medicament for use in the methods.

The invention provides methods for assessing T cell responsiveness to treatment with a lymphocyte depleting therapy in a multiple sclerosis patient, comprising measuring caspase-3 in T cells obtained from said patient after said therapy, wherein an increase in caspase-3 in said T cells compared to T cells from an MS patient not receiving said therapy is indicative of T cell responsiveness to said therapy. The measuring may entail determining the amount or concentration of caspase-3 or nucleic acid encoding caspase-3.

The invention provides methods for informing an MS patient of an increased risk of developing a secondary autoimmune disease following lymphocyte depletion, comprising the steps of obtaining or ascertaining information on interleukin-21 (IL-21) in a blood sample from the MS patient, wherein elevated IL-21 compared to a subject without an autoimmune disease indicates that the patient is at increased risk of developing a secondary autoimmune disease compared to MS patients without elevated IL-21; and informing the patient of an increased risk or lack thereof. Alternatively, the methods comprise obtaining or ascertaining information on the presence or absence of one or more of the aforementioned IL-21 genotypes, instead of information on blood IL-21 level. Accordingly, the invention also provides methods for informing an MS patient of a need, or lack of a need, for heightened monitoring for development of a secondary autoimmune disease following lymphocyte depleting therapy on the basis of the patient's IL-21 level or the presence or absence of the IL-21 genotypes described above.

The invention provides methods for informing a regimen for monitoring an MS patient following lymphocyte depleting therapy, comprising the steps of obtaining or ascertaining information on (i) IL-21 in a blood sample from the patient; or (ii) the presence or absence of one or more genotypes of single-nucleotide polymorphisms (SNPs) associated with elevated IL-21 such as those selected from the group consisting of: A/A at SNP rs13151961, G/G at SNP rs6822844 G/G, and C/C at SNP rs6840978; and selecting a monitoring regimen appropriate for the patient based on the information. An appropriate monitoring regimen may include, for example, measuring auto-antibodies in the patient.

The present invention provides advantages in risk management in MS treatment. For example, the invention provides methods for distributing a lymphocyte depleting drug to a patient for treating multiple sclerosis, comprising the steps of counseling the patient on the increased risk of developing a secondary autoimmune disease following treatment with said drug, wherein the increased risk is associated with (i) elevated IL-21; or (ii) the presence of one or more genotypes of single-nucleotide polymorphisms (SNPs) associated with elevated IL-21 such as those selected from the group consisting of: A/A at SNP rs13151961, G/G at SNP rs6822844 G/G, and C/C at SNP rs6840978; and providing the drug to the patient after said counseling, optionally after obtaining informed consent from the patient.

The invention further provides methods for identifying an individual who is likely to have elevated interleukin-21 (IL-21) compared to a subject without any known inflammatory condition, comprising the step of genotyping the individual to detect the presence or absence of one or more genotypes of single nucleotide polymorphisms (SNPs) associated with elevated IL-21 such as those selected from the group consisting of: A/A at SNP rs13151961, G/G at SNP rs6822844, and C/C at SNP rs6840978, wherein the presence of one or more of said genotypes is associated with elevated IL-21.

In the context of this invention, lymphocyte depletion can be induced by a treatment that targets CD52, e.g., a treatment with an anti-CD52 antibody (e.g., a monoclonal antibody) or an antigen-binding portion thereof. The anti-CD52 antibody can be alemtuzumab or a biologically similar agent such as an antibody that competes for binding to CD52 with alemtuzumab.

In the methods of this invention, IL-21 measurement may entail measuring (e.g., detecting/quantifying) the amount or concentration of IL-21 or nucleic acid encoding IL-21 in a sample, or the amount or concentration of mRNA encoding IL-21 in IL-21-producing cells (e.g., Th17 cells) in the sample. In some embodiments, the measuring is of intracellular IL-21, using, for example, cytokine staining and flow cytometry. In some embodiments, the measuring is of serum IL-21, using, for example, an enzyme-linked immunosorbent assay (ELISA). Also embraced by the invention are ELISA kits for detecting IL-21 levels in a human subject, comprising an anti-IL-21 antibody, or an antigen-binding portion thereof, or a soluble IL-21 receptor. The kits may further include an instruction directing a user to take a blood sample from a human subject.

In the methods of this invention, IL-21 information (including measurement or genotyping) can be obtained prior to, during, or subsequent to MS therapy. The methods of this invention can be used in the context of any MS form, including but not limited to relapsing-remitting multiple sclerosis, primary progressive multiple sclerosis, and secondary progressive multiple sclerosis.

The invention also provides kits for treating multiple sclerosis, comprising a lymphocyte depleting therapeutic agent (e.g., an anti-CD52 antibody such as alemtuzumab); and a written instruction for informing a patient or health care provider of the potential for an increased risk of developing a secondary autoimmune disease following treatment with said agent, wherein the increased risk is indicated by or associated with (i) elevated IL-21, or (ii) the presence of one or more genotypes of single-nucleotide polymorphisms (SNPs) associated with elevated IL-21 such as those selected from the group consisting of: A/A at SNP rs13151961, G/G at SNP rs6822844 G/G, and C/C at SNP rs6840978.

The invention further provides kits for identifying an MS patient who is at increased risk of developing a secondary autoimmune disease following lymphocyte depletion, comprising an anti-interleukin-21 (IL-21) antibody and one or more reagents for detecting the binding of said antibody to IL-21 in a blood sample from the MS patient. The invention also provides kits for identifying an MS patient who is at increased risk of developing a secondary autoimmune disease following lymphocyte depletion, comprising one or more reagents suitable for identifying the genotype of one or more single nucleotide polymorphisms (SNPs) selected from the group consisting of: SNP rs13151961, SNP rs6822844, and SNP rs6840978, in a sample obtained from an individual.

Other features and advantages of the invention will be apparent from the following figures and detailed description.

BRIEF DESCRIPTION OF THE FIGURES

FIG. 1A is a graph showing precursor frequency (PF) of T cells from healthy controls (HC), untreated patients (Pre) and at intervals of 3 months post-alemtuzumab, unstimulated (Unstim), or following culture with myelin basic protein (MBP) or thyroid stimulating hormone receptor (TSHr). (* $p<0.05$,  $p<0.01$, * $p<0.001$)

FIG. 1B is a graph showing proliferative index (PI) of T cells from healthy controls (HC), untreated patients (Pre) and at intervals of 3 months post-alemtuzumab, unstimulated (Unstim), or following culture with myelin basic protein (MBP) or thyroid stimulating hormone receptor (TSHr). (* $p<0.05$,  $p<0.01$, * $p<0.001$)

FIG. 1C is a graph showing the total number of viable T cells after 10 days in culture from healthy controls (HC), untreated patients (Pre) and at intervals of 3 months post-alemtuzumab, unstimulated (Unstim), or following culture with myelin basic protein (MBP) or thyroid stimulating hormone receptor (TSHr). (* $p<0.05$,  $p<0.01$, * $p<0.001$)

FIG. 1D is a graph showing percentage of T cells apoptosing in response to no stimuli or following culture with MBP or TSHr in culture from healthy controls (HC), untreated patients (Pre) and at intervals of 3 months post-alemtuzumab. (* $p<0.05$,  $p<0.01$, * $p<0.001$)

FIG. 5A is a graph showing the proliferative index of unstimulated CD4+ and CD8+ T cells in response to rhIL-21. FIG. 5B is a graph showing the proliferative index of polyclonally stimulated (anti-CD3/CD28) CD4+ and CD8+ T cells in response to rhIL-21. FIG. 5C is a graph showing precursor frequency of unstimulated CD4+ and CD8+ T cells in response to rhIL-21. FIG. 5D is a graph showing precursor frequency of polyclonally stimulated CD4+ and CD8+ T cells in response to rhIL-21. (* p<0.05,  p<0.01, * p<0.001)

FIG. 6A is a graph showing serum IL-21 prior to and after alemtuzumab treatment in 15 patients with, and 15 patients without, secondary autoimmunity. (* p<0.05,  p<0.01, * p<0.001)

FIG. 6B is a graph showing pre-treatment serum IL-21 levels (pg/ml) in the non-autoimmune patients (those who had no post-alemtuzumab autoimmunity) and the autoimmune patients (those who had post-alemtuzumab autoimmunity).

DETAILED DESCRIPTION

Figure 1E:
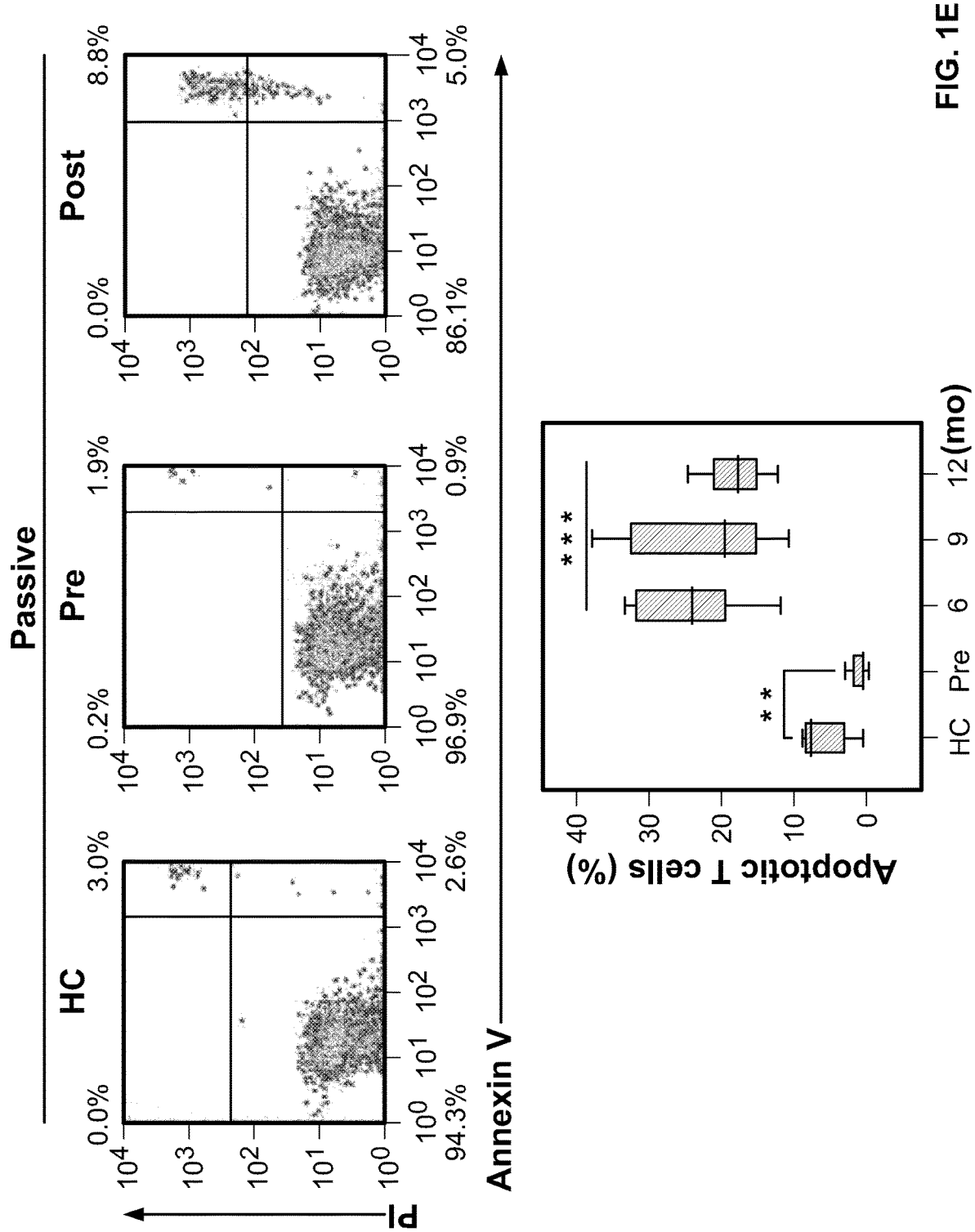
FIG. 1E is plots and a graph showing passive T cell apoptosis from healthy controls and patients before and after alemtuzumab at intervals of 3 months. (* $p<0.05$,  $p<0.01$, * $p<0.001$)

This invention is based on our discovery that the occurrence of secondary autoimmunity in an MS patient following lymphocyte depleting therapy (e.g., after treatment with alemtuzumab) is associated with elevated IL-21 in the patient. We have discovered that IL-21 is elevated compared to the norm (see discussions below) even before the therapy in MS patients who later develop post-therapy secondary autoimmunity. We also have discovered that after lymphocyte depleting therapy, IL-21 is elevated even more dramatically in those same patients, as compared to MS patients with no signs of secondary autoimmunity, whose IL-21 is elevated to a much smaller extent. Thus, IL-21 levels are predictive of the occurrence of secondary autoimmunity after lymphocyte depleting therapy in an MS patient. We also have discovered that single nucleotide polymorphism (SNP) genotypes of A/A at SNP rs13151961, G/G at SNP rs6822844, and C/C at SNP rs6840978 are associated with elevated IL-21 in an individual; thus genotyping an MS patient for the presence or absence of these specific SNP genotypes also helps predict the risk for developing secondary autoimmunity in the patient following lymphocyte depletion.

We first described autoimmunity complicating alemtuzumab (CAMPATH-1H) treatment in 1999 (Coles et al., 1999), and have continued to observe this complication of, what is increasingly recognized as, a highly effective therapy for early relapsing-remitting multiple sclerosis (Coles et al., *J Neurology* 253, 98-108 (2006); Coles et al., 1999 and 2008). Our studies described below involved a series of cohorts of available patients and were aimed at understanding this unprecedented "model" of human autoimmunity occurring in a subset of MS patients treated by alemtuzumab.

The immune state is radically altered following exposure to alemtuzumab. T cells regenerating into the lymphopenic environment generated by alemtuzumab are highly proliferative and skewed towards auto-reactivity. However, these cells are highly unstable and short-lived. Whilst their fate has not previously been directly addressed (King et al., *Cell* 117, 265-277 (2004)), we show that these cells are dying rapidly by apoptosis. High and sustained levels of T cell apoptosis may explain why a single dose of alemtuzumab induces T cell lymphopenia lasting several years even though the half-life of circulating alemtuzumab is only six days and hematological precursors are not depleted (Gilleece et al., *Blood* 82, 807-812 (1993)).

Against that background, we show that patients with secondary autoimmunity have higher rates of T cell apoptosis, but no greater T cell lymphopenia, than those without autoimmunity, suggesting increased cell cycling in this group. These perturbations of T cell cycling are associated with significantly higher serum IL-21 expression, which we have found is genetically determined in at least some cases. Furthermore, susceptibility to lymphopenia-associated autoimmunity is manifest before lymphocyte depletion, with pre-treatment IL-21 levels predicting with accuracy (positive predictive value of more than 70%, e.g., 83%, and negative predictive value of more than 62%, e.g., 72%) the development of autoimmunity months to years after exposure to alemtuzumab. This has significant implications for selecting and managing patients with multiple sclerosis when considering lymphocyte depleting therapy such as a therapy with alemtuzumab. Without wishing to be bound by any theory, we believe that by driving cycles of T cell expansion and death to excess, IL-21 increases the stochastic opportunities for T cells to encounter self-antigen and break tolerance, hence promoting autoimmunity.

In summary, our findings provide the first exploration of lymphopenia-induced autoimmunity in man, and provide a conceptual framework for understanding lymphopenia-associated autoimmunity that goes beyond the narrow context of treating multiple sclerosis with alemtuzumab. The concept is that first therapeutic lymphocyte depletion, and secondly genetically restricted overproduction of IL-21, leads to a state of excess T cell cycling and reduced survival, which promotes autoimmunity in humans. These findings provide bases for the present invention.

This invention provides methods for managing MS patients when considering lymphocyte depleting therapy such as alemtuzumab therapy. For example, our invention provides methods for identifying an MS patient who has elevated IL-21 compared to the norm (i.e., levels of IL-21 in control subject(s) as described below), and methods for identifying an MS patient who is at increased risk of developing secondary autoimmunity following lymphocyte depletion. These methods comprise the step of measuring IL-21 (e.g., intracellular or extracellular protein levels, RNA transcript levels, or IL-21 activity levels; see discussions below) in a blood sample from the patient, and comparing the IL-21 value to the normal IL-21 value. Alternatively, in lieu of or in addition to the blood test, one can genotype the patient for the presence or absence of one or more of SNP genotypes of A/A at SNP rs13151961, G/G at SNP rs6822844, and C/C at SNP rs6840978, where the presence of one, two or all three of these genotypes is associated with elevated IL-21. As discussed above, elevated IL-21 is associated with increased risk of developing secondary autoimmunity in the MS patient following lymphocyte depletion, as compared to MS patients who do not have elevated IL-21.

Identification of a patient by the methods of the invention may be followed by a number of further steps contemplated by the invention. For example, the patient can be informed of the increased risk of developing secondary autoimmunity following lymphocyte depleting therapy, or lack of such risk, based on his/her IL-21 level or genotype. Thus, the invention will allow individualized counseling of the risks of the therapy before commitment to the therapy. The health care provider can consider therapeutic options in view of the risk of secondary autoimmunity and provide a recommendation, including, for example, administering an IL-21 antagonist prior to, during, or after lymphocyte depleting therapy, or selecting a treatment regimen that does not involve lymphocyte depletion.

The health care provider also can consider risk management plans for a patient who elects to undergo lymphocyte depleting therapy. For example, the health care provider can inform the patient of a need for heightened monitoring for development of secondary autoimmunity after lymphocyte depleting therapy in view of his/her increased risk of developing secondary autoimmunity. The health care provider also can recommend an appropriate monitoring regimen following lymphocyte depleting therapy. An appropriate monitoring regimen for patients at risk may include, without limitation, more frequent monitoring for secondary autoimmunity after lymphocyte depleting therapy at an interval of, for example, one week, two weeks, one month, two months, three months, six months, or one year. The monitoring may need to be continued for an extended period of time, for example, more than one year, two years, three years, four years, five years, or more, because some patients may not present with secondary autoimmunity until well after one year following lymphocyte depletion therapy. Heightened monitoring also may entail, for example, more thorough medical examination (e.g., more blood tests) by a specialist for any signs of secondary autoimmunity. Moreover, pharmacists or clinical staff who distribute a lymphocyte depleting drug to a patient for treating MS may be required to counsel the patient on the increased risk of developing secondary autoimmunity following the drug use, in the event that the patient has an elevated level of IL-21 and/or has the particular IL-21 genotypes described herein that have been associated with elevated serum IL-21. The pharmacists or clinical staff may also be required to obtain informed consent from the patient prior to distributing the drug to the patient.

Multiple Sclerosis Patients

The methods and compositions of this invention can be used in the context of any form of MS, for example, relapsing-remitting MS, primary progressive MS, and secondary progressive MS. MS patients in the context of this invention are those who have been diagnosed as having a form of MS by, for example, the history of symptoms and neurological examination with the help of tests such as magnetic resonance imaging (MRI), spinal taps, evoked potential tests, and laboratory analysis of blood samples.

Multiple sclerosis ("MS"), also known as disseminated sclerosis, is an autoimmune condition in which the immune system attacks the central nervous system, leading to demyelination (Compston and Coles, 2008). MS destroys a fatty layer called the myelin sheath that wraps around and electrically insulates nerve fibers. Almost any neurological symptom can appear with the disease, and often progresses to physical and cognitive disability (Compston and Coles, 2008). MS takes several forms. New symptoms can occur in discrete attacks (relapsing forms), or slowly accumulate over time (progressive forms) (Lublin et al., *Neurology* 46 (4), 907-11 (1996)). Between attacks, symptoms may go away completely (remission), but permanent neurological problems often occur, especially as the disease advances (Lublin et al., 1996). Several subtypes, or patterns of progression, have been described, and they are important for prognosis as well as therapeutic decisions. In 1996 the United States National Multiple Sclerosis Society standardized four subtype definitions: relapsing-remitting, secondary progressive, primary progressive, and progressive relapsing (Lublin et al., 1996).

The relapsing-remitting subtype is characterized by unpredictable acute attacks, called exacerbations or relapses, followed by periods of months to years of relative quiet (remission) with no new signs of disease activity. This describes the initial course of most individuals with MS (Lublin et al., 1996).

Secondary progressive MS begins with a relapsing-remitting course, but subsequently evolves into progressive neurologic decline between acute attacks without any definite periods of remission, even though occasional relapses and minor remissions may appear (Lublin et al., 1996).

The primary progressive subtype is characterized by a gradual but steady progression of disability with no obvious remission after their initial MS symptoms appear (Miller et al., *Lancet Neurol* 6 (10), 903-12 (2007)). It is characterized by progression of disability from onset, with no, or only occasional and minor, remissions and improvements (Lublin et al., 1996). The age of onset for the primary progressive subtype is usually later than other subtypes (Miller et al., 2007)).

Progressive relapsing MS is characterized by a steady neurological decline with acute attacks that may or may not be followed by some recovery. This is the least common of all the subtypes described hereinabove (Lublin et al., 1996).

Cases with non-standard behavior have also been described, sometimes referred to as borderline forms of MS (Fontaine, *Rev. Neurol.* (Paris) 157 (8-9 Pt 2): 929-34 (2001)). These forms include Devic's disease, Balo concentric sclerosis, Schilder's diffuse sclerosis, and Marburg multiple sclerosis (Capello et al., *Neurol. Sci.* 25 Suppl 4: S361-3 (2004); Hainfellner et al., *J. Neurol. Neurosurg. Psychiatr.* 55 (12): 1194-6 (1992)).

Lymphocyte Depletion in Multiple Sclerosis Patients

As used herein, "lymphocyte depletion" is a type of immunosuppression by reduction of circulating lymphocytes, e.g., T cells and/or B cells, resulting in lymphopenia. Prolonged lymphocyte depletion is seen when, for example, autologous bone marrow transplantation (BMT) or total lymphoid irradiation is used to treat multiple sclerosis. See, e.g., Cox et al., *Eur. J. Immunol.* 35, 3332-3342 (2005). For example, lymphocyte depletion can be achieved by a combined use of thymoglobulin, cyclophosphamide and whole body irradiation. Lymphocyte depletion in MS patients also can be achieved by a number of drug treatments. For example, a humanized anti-CD52 monoclonal antibody, CAMPATH-1H (alemtuzumab), has been used in lymphocyte depleting therapy to treat MS patients. CAMPATH-1H-induced lymphopenia has been shown to effectively reduce central nervous system inflammation both clinically and radiologically (Coles et al., *Ann. Neurol.* 46, 296-304 (1999); Coles et al., 2008).

Other agents can also be used in lymphocyte depleting therapy to treat MS patients. These agents can be those that cause lymphocyte cell death or inhibit lymphocyte functions. They include, without limitation, (1) agents targeting CD-52-bearing cells, such as agents biologically similar to alemtuzumab, i.e., other anti-CD52 antibodies (e.g., chimeric, humanized, or human antibodies) that bind to the same or a different epitope as alemtuzumab or compete with alemtuzumab for binding to CD52, and soluble CD52 polypeptides that compete with cell surface CD52 for binding to ligand(s) of CD52; (2) biomolecules such as peptides, proteins, and antibodies (e.g., chimeric, humanized, or human antibodies) that target cell-surface molecules on lymphocytes, such as anti-CD4 antibodies, anti-CD20 antibodies (e.g., rituximab), anti-TCR antibodies, and anti-integrin antibodies (e.g., natalizumab); (3) cytotoxins (e.g., apoptosis-inducing agents, cyclophosamide, alkylating agents, and DNA intercalators) delivered specifically or nonspecifically to lymphocytes; and (4) antigen-binding portions of the aforementioned antibodies. The antibodies may include, without limitation, monoclonal antibodies, bifunctional antibodies, oligoclonal antibodies, and polyclonal antibodies.

The term "antigen-binding portion" as used herein refers to one or more fragments of an antibody that retain the ability to specifically bind to the same antigen as the whole antibody from which the portion is derived. Examples of "antigen-binding portion" include, without limitation, a Fab fragment, a F(ab')2 fragment, a Fd fragment, a Fv fragment, a dAb fragment, an isolated complementarity determining region (CDR), scFv, and a diabody. The antibodies and antigen-binding portions thereof useful in this invention can be made by any methods well known in the art. Any of the above lymphocyte depleting therapies can cause lymphopenia, and in some patients, the lymphopenia leads to secondary autoimmunity.

Secondary Autoimmunity in MS Patients

Autoimmunity is referred to herein as "secondary autoimmunity" when it arises subsequent to the onset of a first ("primary") disease, for example, a "primary" autoimmune disease. Secondary autoimmunity sometimes arises in MS patients having, or having had, lymphopenia following, e.g., lymphocyte depleting therapy. In some individuals, secondary autoimmunity arises soon after lymphocyte depleting therapy (e.g., treatment with alemtuzumab). In other individuals, secondary autoimmunity may not arise until months or years after lymphocyte depleting therapy; in some of those individuals, by the time they develop secondary immunity, substantial lymphocyte recovery (total lymphocyte count) may have occurred so that they may no longer be lymphopenic.

Secondary autoimmunity arising in lymphopenic MS patients can be any type of autoimmune condition other than MS, including but not limited to thyroid autoimmunity (e.g., Graves' disease), immune thrombocytopenia (ITP), Goodpasture's disease, autoimmune neutropenia, autoimmune hemolytic anemia, and autoimmune lymphopenia. Techniques for diagnosing and monitoring these autoimmune diseases are well known to those skilled in the art, including assessment of symptoms and medical examination such as blood analysis. The invention contemplates the use of any known methods. For example, autoantibody levels in a patient's body fluid (e.g., blood) can be determined as a means of detecting signs of autoimmunity. Specifically, anti-nuclear antibodies, anti-smooth muscle antibodies, and anti-mitochrondrial antibodies can be measured. In the event anti-nuclear antibodies are detected, additional assays can be performed to measure anti-double-stranded DNA antibodies, anti-ribonucleoprotein antibodies, and anti-La antibodies. Anti-thyroid peroxidase (TPO) and anti-thyroid stimulating hormone (TSH) receptor antibodies can be measured to detect autoimmune thyroid diseases; if anti-TPO or anti-TSH receptor antibodies are detected, one can measure whether thyroid function is affected by measuring free T3, free T4 and TSH levels. Anti-platelet antibodies can be measured to detect autoimmune thrombocytopenia; and a measurement of blood platelet levels may serve to determine if the presence of anti-platelet antibodies is causing a reduction in platelet number.

Measurement of IL-21

In the methods of this invention, IL-21 can be measured by a number of techniques. IL-21 is a member of the gamma-c-related cytokine family, and has potent activity in promoting T and B cell proliferation and natural killer (NK) cell cytotoxicity. IL-21 is mainly expressed by activated CD4+ T cells (e.g., Th17 cells) and is important in T helper type I (Th1) immune responses (Weiss et al., *Expert Opin Biol. Ther.* 7, 1705-1721 (2007); Sivakumar et al., *Immunology* 112, 177-182 (2004)). The human IL-21 gene encodes a polypeptide precursor of 162 amino acid residues and a fully processed mature protein of 133 amino acid residues (about 15 kD); the gene is located on human chromosome 4q26-27 (Sivakumar et al., 2004). The receptor for IL-21 (IL-21R) has been found on resting peripheral B cells, activated peripheral blood mononuclear cells, and in germinal center of human lymph nodes (Marleau et al., *J. Leukocyte Biol.* 78, 575-584 (2005)).

Methods of measuring IL-21 are well known to those skilled in the art. According to some embodiments of the present invention, a body fluid sample (e.g., blood, serum, plasma, urine, saliva, or cerebrospinal fluid) is obtained from a patient, and the IL-21 level in the sample is measured, by any assay suitable for protein detection, including but not limited to, immunoassays such as enzyme-linked immunosorbent assays (ELISA). Commercial ELISA kits for measuring human IL-21 are available from, for example, KOMABIOTECH (Seoul, Korea), Bender MedSystems (Burlingame, Calif.), and eBioscience (San Diego, Calif.).

Alternatively, IL-21 transcript levels in IL-21 producing cells (e.g., Th17 cells) obtained from the patient can be measured by Northern blot analysis and quantitative polymerase chain reaction (Q-PCR). Methods of isolating Th17 cells are well known in the art, and isolation can be done by using commercially available kits, e.g., kits from Miltenyi Biotec (Auburn, Calif.), eBioscience (San Diego, Calif.). In some embodiments, IL-21 levels are measured by cytokine staining and flow cytometry in which an anti-IL-21 antibody linked to a detectable moiety is used to detect the intracellular level of IL-21 in IL-21 producing cells from the patient. IL-21 also can be measured in terms of activity in a biological assay, e.g., by measuring proliferative responses of T cells to a combination of IL-21 and IL-15 using, e.g., CFSE (carboxyfluorescein succinimidyl ester) (Zeng et al., *Curr. Protoc. Immunol.* 78:6.30.1-6.30.8 (2007)). Another method of measuring IL-21 is based on IL-21-induced tyrosine phosphorylation of Stat3 in splenic CD8(+) T cells using a flow cytometry-based analysis (Zeng et al., 2007). Those of skill in the art will readily appreciate other suitable means for measuring IL-21.

In the methods of this invention, the reference (or index) value for determining whether a patient has elevated (abnormally high) IL-21 is the value of IL-21 of a control subject, or the mean value of IL-21 of a group of control subjects, obtained using the same assay that is conducted at the same or a different time. The control subject is a normal or healthy subject, who, in this context, is an individual without any ongoing known inflammatory condition, including without an autoimmune disease (without any detectable symptoms of an autoimmune disease). In some embodiments, the control subjects are not lymphopenic. An increase of IL-21 level by about 10%, 20%, 30%, 40%, 50%, 100%, two-fold, three-fold, four-fold, five-fold, ten-fold, twenty-fold, thirty-fold, forty-fold, fifty-fold, one hundred-fold or more may be considered a significant increase. Certain statistical analyses can be applied to determine if the IL-21 level in a test sample is significantly different from the control level. Such statistical analyses are well known to those skilled in the art and may include, without limitation, parametric (e.g., two-tailed Student's t-test) or non-parametric (e.g., Wilcoxon-Mann-Whitney U test) tests.

Detecting IL-21 SNP Genotypes

In some methods of this invention, genotyping is used to predict whether a patient is prone to having (i.e., at risk of having or likely to have) elevated IL-21 and hence at risk of developing secondary autoimmunity while having lymphopenia. "Genotyping" refers to the process of determining the genotype of an individual by the use of biological assays. Methods of genotyping are well known to those skilled in the art, and include, without limitation, PCR, DNA sequencing, allele-specific oligo (ASO) probes, and hybridization to DNA microarrays or beads. Genotyping can be partial, i.e., only a small fraction of an individual's genotype is determined. In the context of this invention, only certain SNPs need to be detected. A SNP is a DNA sequence variation occurring when a single nucleotide—A, T, C, or G—in a corresponding portion of the genome differs between members of a species or between paired chromosomes in an individual. Known human SNPs are assigned reference SNP (refSNP or rs) identification numbers in the public-domain archive Single Nucleotide Polymorphism Database (dbSNP) hosted at the National Center for Biotechnology Information (NCBI).

The present inventors have discovered that the minor SNP genotypes of rs13151961 A/A, rs6822844 G/G and rs6840978 C/C are associated with significantly higher levels of serum IL-21 compared to individuals who do not have these genotypes. MS patients having one or more of these SNP phenotypes, thus, have an increased susceptibility to developing secondary autoimmunity after lymphocyte depletion, compared to MS patients who do not have these genotypes.

Timing of Obtaining IL-21 Information

Obtaining information on IL-21 (IL-21 levels or IL-21-related SNP genotypes) of an MS patient is useful in selecting treatment and post-treatment monitoring regimens for the patient. When the information is obtained prior to MS therapy, the patient can be informed of the relative risk of developing secondary autoimmunity following lymphocyte depleting therapy and treatment decisions can be made accordingly. The patient also can be informed of a need for heightened post-treatment monitoring, e.g., more frequent and more thorough examination by a specialist, if he is classified as "at risk." Thus, the IL-21 information improves risk management (by physicians, pharmacists, and patients) in MS treatment.

Obtaining IL-21 information during or after MS treatment also will be helpful in monitoring secondary autoimmunity development and treatment. As noted above and further described below, we have discovered that following lymphocyte depleting therapy, MS patients who go on to develop secondary autoimmunity have a much larger increase in their serum IL-21, as compared to MS patients who do not develop secondary autoimmunity. The latter group of MS patients produce only slightly more IL-21 following lymphocyte depletion. Thus, by measuring IL-21 production after lymphocyte depleting treatment, one also can predict the risk of secondary autoimmunity, which may not occur until months or years after the treatment.

Treating Secondary Autoimmunity

A secondary autoimmunity disease arising in MS patients can be treated based on the type of the disease. In some embodiments of the present invention, the secondary autoimmunity can be treated by using an effective dose of an IL-21 antagonist. An IL-21 antagonist can be a therapeutic agent that inhibits IL-21 activity, e.g., an agent that inhibits the interaction between IL-21 and IL-21R. "An effective dose" refers to the amount of an inhibiting agent sufficient to inhibit IL-21 activity in a patient such that symptoms of the secondary autoimmune disease are alleviated or prevented. IL-21 antagonists can be, for example, chimeric, humanized, or human monoclonal antibodies to human IL-21 or IL-21R, or soluble IL-21R proteins. See also, e.g., U.S. Pat. No. 7,410,780 and U.S. Patent Application Publication No. 20080241098, the entire teachings of which are incorporated herein by reference. Pharmaceutical compositions containing an IL-21 antagonist can be made according to methods known to those in the art. Pharmaceutical compositions containing IL-21 antagonists can be administered to a patient using a suitable method known in the art, e.g., intravenously, intramuscularly, or subcutaneously.

Kits for Treating and Testing MS Patients

The present invention provides kits for treating multiple sclerosis. A kit of this invention can contain, inter alia, a lymphocyte depleting drug (e.g., alemtuzumab), and a written instruction for informing a patient or a healthy care provider of contraindications of the drug, for example, the potential for an increased risk of developing a secondary autoimmune disease following treatment with the drug. The increased risk can be associated with or indicated by (i) elevated IL-21, or (ii) the presence of one or more genotypes of single-nucleotide polymorphisms (SNPs) selected from the group consisting of: A/A at SNP rs13151961, G/G at SNP rs6822844, and C/C at SNP rs6840978.

In other embodiments, the invention provides kits for detecting serum IL-21 in an MS patient, and/or for identifying MS patients at increased risk of developing a secondary autoimmune disease following lymphocyte depletion. Such kits can comprise an anti-IL-21 antibody, or an antigen-binding portion thereof, or a soluble IL-21 receptor, and optionally an instruction directing a user to take a blood sample from a patient, and optionally one or more reagents for detecting the binding of the antibody, portion, or soluble IL-21 receptor to IL-21 in the blood sample from the MS patient. Such kits will have been validated or approved by an appropriate regulatory authority for making medical diagnosis in patients, such as MS patients.

In still other embodiments, the invention provides kits for identifying an MS patient who is at increased risk of developing a secondary autoimmune disease following lymphocyte depletion. The kits can comprise one or more reagents suitable for identifying the presence or absence of one or more SNP genotypes selected from the group consisting of: SNP rs13151961, SNP rs6822844, and SNP rs6840978, in a sample obtained from an MS patient, and an instruction directing a user to take a sample from an MS patient.

Assessing T Cell Responsiveness to MS Treatment

This invention provides methods for assessing T cell responsiveness to treatment with lymphocyte depleting therapy in an MS patient. The methods entail measuring caspase-3 in T cells obtained from the patient after the treatment. An increase in caspase-3 (e.g., caspase-3 protein, RNA transcript, and/or activity levels) in the T cells compared to T cells from an MS patient not receiving the treatment indicates that the T cells in the treated patient have responded to the treatment. These methods are based on our discovery that T cells from people with untreated MS are apoptosis-resistant, and that this resistance is associated with under-expression of caspase-3. But after lymphocyte depleting therapy, caspase-3 expression is significantly increased in T cells, reaching levels seen in healthy people.

Techniques of measuring caspase-3 in T cells are well known in the art. For example, one can obtain cell extracts from T cells using techniques well known in the art, and measure caspase-3 protein levels by, e.g., ELISA. Commercial ELISA kits for measuring human caspase-3 are available from, e.g., Bender MedSystems (Burlingame, Calif.), EMD Chemicals, Inc. (San Diego, Calif.), and R&D Systems, Inc. (Minneapolis, Minn.). Alternatively, caspase-3 transcript levels can be measured in T cells by, for example, Northern blot analysis or quantitative PCR. Caspase-3 can also be measured in terms of activity in a biological assay, e.g., by measuring its protease activity. Commercial kits for measuring caspase-3 activity are available from, e.g., Roche Applied Science (Indianapolis, Ind.), and Invitrogen (Carlsbad, Calif.).

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and embodiments, the word "comprise," or variations such as "comprises" or "comprising" will be understood to imply the inclusion of a stated integer or group of integers but not the exclusion of any other integer or group of integers. The materials, methods, and examples are illustrative only and not intended to be limiting.

The following examples are meant to illustrate the methods and materials of the present invention. Suitable modifications and adaptations of the described conditions and parameters normally encountered in the art which are obvious to those skilled in the art are within the spirit and scope of the present invention.

EXAMPLES

In the following examples, all patients had relapsing-remitting multiple sclerosis and were participants in one of two clinical trials: CAMMS-223 and CAMMS-224 (REC 02/315 and 03/078) in which alemtuzumab was given by intravenous infusion of 12-24 mg/day for five days, followed by re-treatment at 12 months. Patients and controls consented to venesection for research purposes (LREC 02/263) and all were free from exposure to other disease modifying agents, including steroids, for at least one month at the time of blood sampling.

Lymphocyte proliferation and apoptosis data were generated by a cross-sectional study of fresh, ex vivo cells from 65 patients and 21 healthy controls (7 males, mean age 34 years). This generated hypotheses about T-cell cycling in the pathogenesis of secondary autoimmunity, which were tested on samples available at nine months after alemtuzumab treatment, which was chosen as the earliest time point in which T cell apoptosis could be robustly analyzed. Of the 29 samples available at this time point, 10 met our study definition of autoimmunity (1 male, mean age 36 years) compared to 10 without autoimmunity (3 male, mean age 38 years). Autoimmunity was defined as development of a novel autoimmune disease (with or without autoantibodies), or persistent significant titers of autoantibodies (present on at least two occasions at least three months apart) without clinical disease. "No autoimmunity" was defined as the absence of an autoimmune disease and autoantibodies for at least 18 months post-alemtuzumab in this study. Of the ten patients with autoimmunity, three had autoantibodies only (antinuclear antibodies). Next, serum IL-21 was measured serially in: 15 randomly selected patients with autoimmunity—five of whom had been studied as above (three males, mean age 34 years; twelve with thyroid autoimmunity, one with Goodpasture's disease, one with ITP, and one with antinuclear antibodies only), and fifteen randomly selected patients without autoimmunity—six of whom had been studied as above, (five males, mean age 31 years) and nineteen healthy controls (seven male, mean age 33 years).

73 subjects were studied for genetic analysis. Of these, 23 met the definition of "no autoimmunity" and 27 had secondary autoimmunity after alemtuzumab (six with autoantibodies only: four with antinuclear and two with anti-smooth muscle antibodies; eighteen with thyroid autoimmunity, two with ITP and one with Goodpasture's disease). The 23 remaining subjects could not be categorised on the basis of transient autoantibody production and/or insufficient time since treatment with alemtuzumab.

For all the statistical analysis described in the following examples, data were analyzed using SPSS 12.0.1 for Windows. Following assessment for normality, parametric (Student's t-test) or non-parametric (Wilcoxon-Mann-Whitney) tests were performed. P values are stated throughout the text, where a value of $p<0.05$ was considered as statistically significant, modified by a Bonferroni correction where indicated.

Example 1: Alemtuzumab Induces a T Cell Lymphopenia

A single dose of alemtuzumab resulted in the depletion of CD4+ and CD8+T lymphocytes to 5.6% and 6.8% respectively of baseline values at month 1, and 30.3% and 40.8% respectively at month 12 (data not shown).

Example 2: T Cells from Patients with Untreated Multiple Sclerosis are Resistant to Cell Death For various assays performed in this Example, different cross-sectional and longitudinal samples were used according to availability. As a prelude to measuring lymphocyte cell cycling after alemtuzumab, we examined the proliferative response of T cells, unstimulated or in culture with myelin basic protein (MBP) or the thyroid-stimulating hormone receptor (TSHr), between untreated patients with multiple sclerosis and normal controls (FIGS. 1A and 1B).

A. Peripheral Mononuclear Cell Cultures

Peripheral blood mononuclear cells (PBMCs) were isolated from heparinized blood by centrifugation on a Ficoll-Paque density gradient (Amersham Pharmacia Biotech). Whole PBMCs were immediately suspended in culture medium (RPMI) containing 1% penicillin, 1% streptomycin and 10% fetal calf serum (Sigma 55394) and adjusted to a concentration of $10^6$/mL viable cells (determined by trypan blue exclusion). To induce passive cell death, PBMCs were incubated for 72 hours in media alone without additional growth factors. Fas-mediated apoptosis was induced by culturing PBMCs for 48 hours with soluble anti-CD28 (1 μg/mL: kindly donated by M. Frewin, University of Oxford) in anti-CD3 mAb-precoated plates (1 μg/mL—BD Pharmingen), followed by 18 hours incubation with activating anti-human Fas (clone CH11, 1 μg/mL—Upstate Biotechnology, Lake Placid, N.Y.).

B. Detection of Apoptosis

Apoptotic T cells were detected by staining cells with: allophycocyanin-conjugated mouse anti-human monoclonal antibodies against CD3 (Serotec MCA463APC), CD4 (Serotec MCA1267APC) and CD8 (Serotec MCA1226APC), FITC-conjugated annexin-V and Propidium Iodide (BD Pharmingen). Fluorescence was detected by flow cytometry (FACSCALIBUR: Becton Dickinson, Mountain View, Calif.). Based on forward and side scatter, a wide lymphocyte gate was drawn to include live and apoptotic lymphocytes (having reduced FSc and increased SSc). At least 15,000 events within the gate were collected and analyzed using WinMDI 2.8 software. Early apoptotic cells were defined as annexinV$^+$PI$^-$, and late apoptotic or necrotic cells as annexinV$^+$PI$^+$ (Aubry et al., *Cytometry* 37, 197-204 (1999)). Apoptotic cell death was defined as total cell death (annexinV$^+$PI$^-$ plus annexinV$^+$PI$^+$) blocked by pan-caspase inhibition with Q-VD-OPh (RnD Systems OPH001).

C. Proliferation Assays

PBMCs were loaded with the cell division tracking dye CFSE (carboxyfluorescein diacetate succinimidyl ester) (Lyons et al. *Methods Cell Biol.* 63, 375-398 (2001)) and cultured with 50 μg/mL myelin basic protein (MBP: RDI-TRK8M79/LYO) or 1 μg/mL thyroid stimulating hormone receptor extracellular domain bound to a matrix binding protein (TSHr: kindly donated by M. Ludgate, Cardiff University). After 10 days CFSE staining in cells, identified by specific surface markers (CD4, CD8), was analysed by flow cytometry. Precursor frequency (defined as the proportion of lymphocytes that left the parent population to undergo at least two cell divisions) and proliferation index (defined as the sum of the cells in all generations divided by the computed number of parent cells) were calculated using Modfit LT 3.0 (Verity Software). Absolute number of surviving cells was measured by comparison with a fixed number of inert beads (BD CALIBRITE, BD Biosciences), included in cultures.

D. Results

Figure 1F:
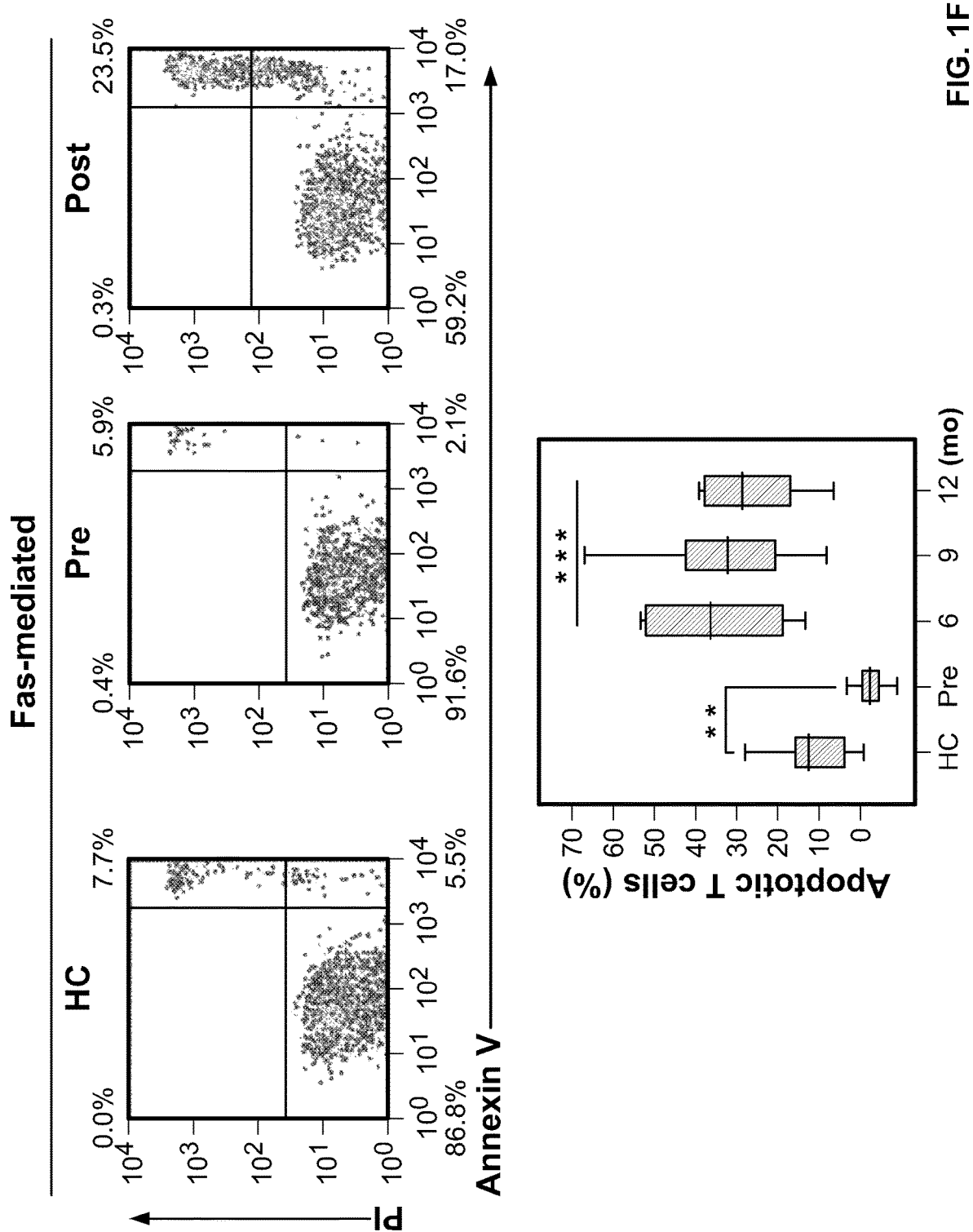
FIG. 1F is plots and a graph showing Fas-mediated T cell apoptosis from healthy controls and patients before and after alemtuzumab at intervals of 3 months. (* $p<0.05$,  $p<0.01$, * $p<0.001$)

There was no difference in the proliferative response of T cells, unstimulated or in culture with myelin basic protein (MBP) or the thyroid stimulating hormone receptor (TSHr), between untreated patients with multiple sclerosis and normal controls (FIGS. 1A and 1B). Conversely, survival of T cells from untreated patients with multiple sclerosis was ≥4 fold greater than that of controls (p<0.005; FIG. 1C), suggesting that reduced T cell death is a feature of untreated multiple sclerosis. We confirmed this by demonstrating that T cells from untreated patients are resistant both to passive and Fas-mediated apoptosis compared with healthy controls (passive: 0.3% v. 6.7%, p=0.0016; and Fas-mediated: 2.9% v. 15.5%, p=0.0018; FIGS. 1E and 1F).

Figures 1G, 1H:
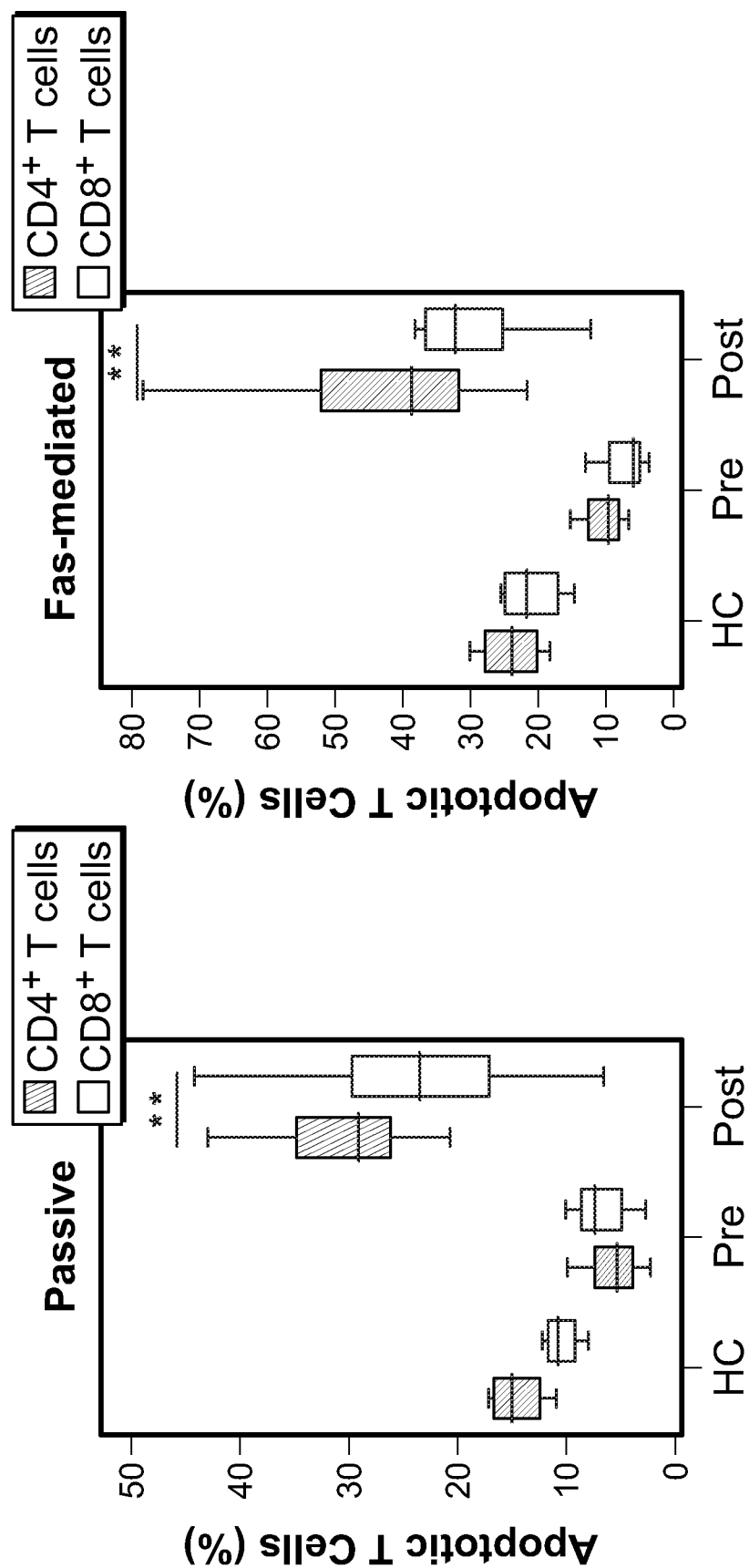
FIG. 1G is a graph showing passive CD4+ and CD8+ T cell apoptosis from healthy controls, pre-treatment patients and at 9 months post-alemtuzumab. (* $p<0.05$,  $p<0.01$, * $p<0.001$)
FIG. 1H is a graph showing Fas-mediated CD4+ and CD8+ T cell apoptosis from healthy controls, pretreatment patients and at 9 months post-alemtuzumab. (* $p<0.05$,  $p<0.01$, * $p<0.001$)

Example 3: T Cells that Regenerate after Alemtuzumab are Highly Proliferative, Skewed Towards Self Reactivity and Susceptible to Apoptosis Using the assays described in Example 2, we found that following alemtuzumab, the proportion of T cells responding to self-antigens (precursor frequency) and the degree of proliferation (proliferative index) were significantly increased compared to untreated patients and healthy controls. For example at month 3, unstimulated T cell proliferation was >6.5 fold that of untreated patients and proliferation in response to MBP and TSHr stimulation was increased by 900% and 700% respectively (all p<0.01: FIGS. 1A and 1B). T cell apoptosis was also significantly increased post-alemtuzumab. In response to antigenic stimulation, the proportion of T cells undergoing apoptosis at six months was 10 fold greater than at baseline (FIG. 1D; p<0.001 for all antigens) resulting in fewer viable T cells at the end of culture (FIG. 1C). Passive and Fas-mediated apoptosis were also increased after alemtuzumab, with rates at least double those observed in the healthy control group (passive: 24.5%, 22.2% and 17.9% at 6, 9 and 12 months, respectively, compared to 6.7% in controls, all p<0.001; Fas-mediated 37.8%, 35.8% and 29.9% at 6, 9 and 12 months, respectively, compared to 15.5% in controls, all p<0.01; FIGS. 1E and 1F). Increased lymphocyte apoptosis after alemtuzumab was seen in both the CD4+ and CD8+ subpopulations (FIGS. 1G and 1H) and persisted for at least 18 months after alemtuzumab treatment (data not shown).

Example 4: T Cells from Untreated Patients with Multiple Sclerosis Under-Express Caspase 3

A. mRNA Analysis

PBMCs, immediately ex-vivo or after culture with MBP or polyclonal stimulation, were positively separated, using 20 μL of magnetic beads (Miltenyi Biotec; CD19 Microbeads, CD3 Microbeads, CD14 Microbeads) per 1×10$^7$ cells loaded into a MACS® LS Column. Magnetically retained cells were eluted, washed and stored in RNAlater™ at −70° C. (cell purity consistently 95-98%, data not shown).

Fas, FasL, Bcl-2, Bcl-X1, Bad, Bax, Bid, Bim, Survivin, c-FLIP, and Caspase 3, 8 and 9 expression was determined by semi-quantitative RT-PCR. mRNA was extracted from cells stored in RNAlater™ using the RNEASY Mini Kit (QIAgen) and reverse transcribed to cDNA using the PROSTAR First Strand RT-PCR Kit (Stratagene). PCR primers and probes were designed using PRIMER EXPRESS (PE Biosystems, Foster City, Calif., USA), and purchased from Oswel DNA service. mRNA sequence information was obtained from GenBank. Quantitative real-time PCR was performed on an ABI Prism 7900HT Sequence Detection System (Perkin Elmer) using PCR Mastermix containing ROX (Eurogentec RT-QP2X-03). Primer and probe sequences were: Bcl-2 For: 5'-CCT GTG GAT GAC TGA GTA CCT GAA-3' (SEQ ID NO:1), Rev 5'-CAC CTA CCC AGC CTC CGT TA-3' (SEQ ID NO:2), JOE-labelled probe 5'-CGG CAC CTG CAC ACC TGG ATC-3' (SEQ ID NO:3); Bcl-Xl For 5'-TTC AGT CGG AAA TGA CCA GAC A-3' (SEQ ID NO:4), Rev 5'-GAG GAT GTG GTG GAG CAG AGA-3' (SEQ ID NO:5), FAM-labelled probe 5'-TGA CCA TCC ACT CTA CCC TCC CAC CC-3' (SEQ ID NO:6); Fas For 5'-AAA AGC ATT TTG AGC AGG AGA GTA TT-3' (SEQ ID NO:7), Rev 5'-GGC CAT TAA GAT GAG CAC CAA-3' (SEQ ID NO:8), JOE-labelled probe 5'-CTA GAG CTC TGC CAC CTC TCC ATT-3' (SEQ ID NO:9); FasL For 5'-AAG AAA GTG GCC CAT TTA ACA G-3' (SEQ ID NO:10), Rev 5'-AGA AAG CAG GAC AAT TCC ATA GGT-3' (SEQ ID NO:11), FAM-labelled probe 5'-CAA CTC AAG GTC CAT GCC TCT GG-3' (SEQ ID NO:12); Survivin For 5'-CTG CCT GGC AGC CCT TT-3' (SEQ ID NO:13), Rev 5'-CTC CAA GAA GGG CCA GTT CTT-3' (SEQ ID NO:14), FAM-labelled probe 5'-TCA AGG ACC ACC GCA TCT CTA CAT T-3' (SEQ ID NO:15); c-FLIP For 5'-GTG GAG ACC CAC CTG CTC-3' (SEQ ID NO:16), Rev 5'-GGA CAC ATC AGA TTT ATC CAA ATC C-3' (SEQ ID NO:17), FAM-labelled probe 5'-CTG CCA TCA GCA CTC TAT AGT CCG AAA CAA-3' (SEQ ID NO:18); Caspase 8 For 5'-AGG AGG AGA TGG AAA GGG AAC TT-3' (SEQ ID NO:19), Rev 5'-ACC TCA ATT CTG ATC TGC TCA CTT CT-3' (SEQ ID NO:20), JOE-labeled probe 5'-CTC CCT ACA GGG TCA TGC TCT ATC AGA TTT CAG-3' (SEQ ID NO:21); Caspase 3 For 5'-AAG ATC ATA CAT GGA AGC GAA TCA-3' (SEQ ID NO:22), Rev 5'-CGA GAT GTC ATT CCA GTG CTT TTA-3' (SEQ ID NO:23), FAM-labeled probe 5'-CTG GAA TAT CCC TGG ACA ACA GTT ATA AA-3' (SEQ ID NO:24); Caspase 9 For 5'-TGC GAA CTA ACA GGC AAG CA-3' (SEQ ID NO:25), Rev 5'-GAA CCT CTG GTT TGC GAA TCT C-3' (SEQ ID NO:26), FAM-labeled probe 5'-CAA AGT TGT CGA AGC CAA CCC TAG AAA ACC TTA-3' (SEQ ID NO:27); Bad For 5'-CAG TGA CCT TCG CTC CAC ATC-3' (SEQ ID NO:28), Rev 5'-ACG GAT CCT CTT TTT GCA TAG-3' (SEQ ID NO:29), JOE-labeled probe 5'-ACT CCA CCC GTT CCC ACT GCC C-3' (SEQ ID NO:30); Bax For 5'-TTT CTG ACG GCA ACT TCA ACT-3' (SEQ ID NO:31), Rev 5'-GGT GCA CAG GGC CTT GAG-3' (SEQ ID NO:32), JOE-labeled probe 5'-TGT CGC CCT TTT CTA CTT TGC CAG CA-3' (SEQ ID NO:33); Bid For 5'-GCT GTA TAG CTG CTT CCA GTG TAG-3' (SEQ ID NO:34), Rev 5'-GCT ATC TTC CAG CCT GTC TTC TCT-3' (SEQ ID NO:35), JOE-labeled probe 5'-AGC CCT GGC ATG TCA ACA GCG TTC-3' (SEQ ID NO:36) and Bim For 5'-ACC ACA AGG ATT TCT CAT GAT ACC-3' (SEQ ID NO:37), Rev 5'-CCA TAT GAC AAA ATG CTC AAG GAA-3' (SEQ ID NO:38), FAM-labeled probe 5'-TAG CCA CAG CCT CTC CT-3' (SEQ ID NO:39).

B. Results

Figures 2A, 2B, 2C:
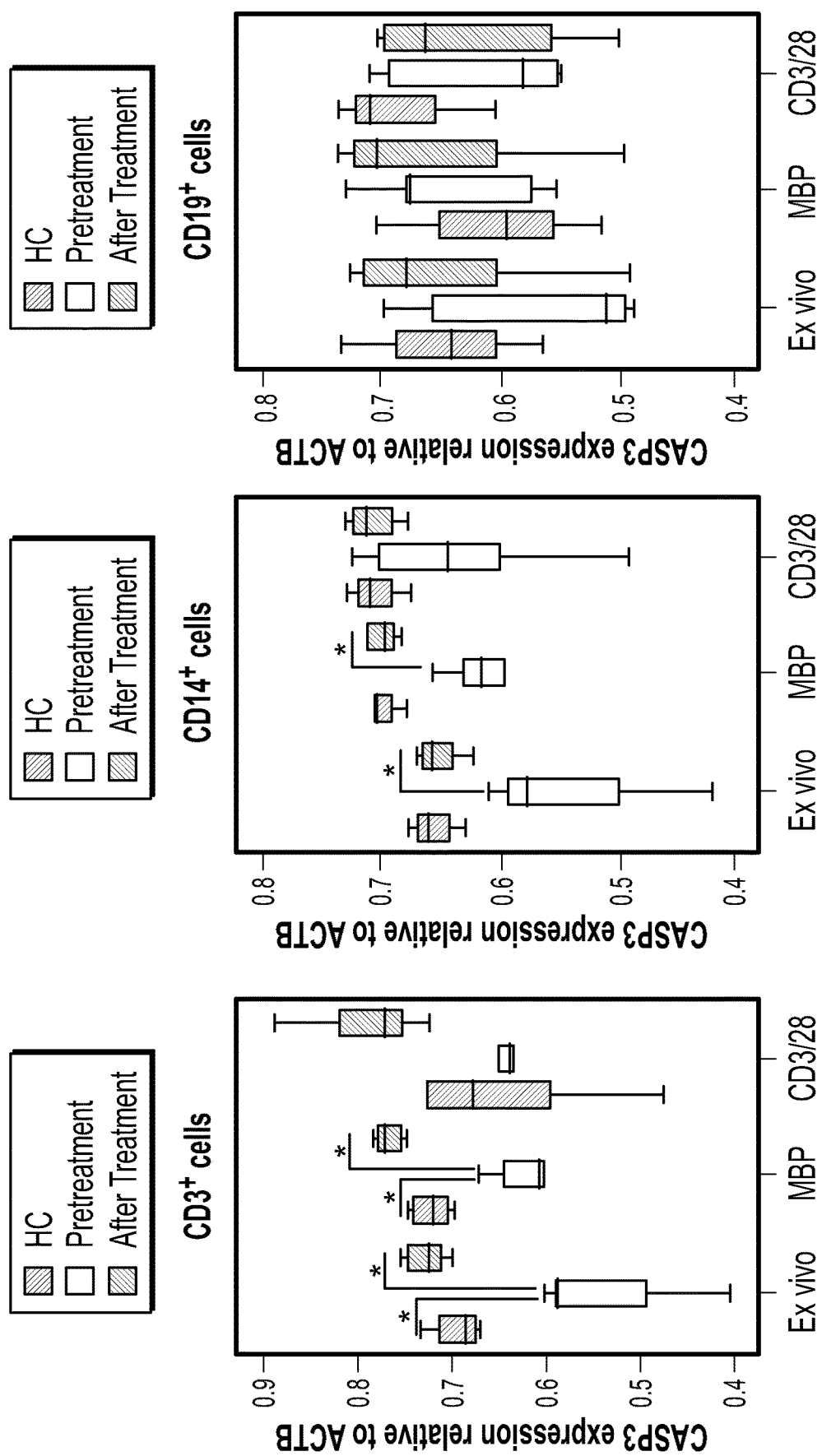
FIGS. 2A-2C are graphs showing caspase 3 mRNA expression relative to beta-actin mRNA expression in (A) CD3+ T cells, (B) CD14+ monocytes, and (C) CD19+ B cells, respectively, either immediately ex-vivo or following stimulation with MBP or polyclonal stimulation (anti-CD3/28 antibodies). (* p<0.05,  p<0.01, * p<0.001)

T cell mRNA expression of caspase 3, the effector caspase common to both apoptotic pathways, from untreated multiple sclerosis patients was reduced compared to controls; this was significant for unstimulated and MBP-stimulated PBMCs (by 78% and 87% respectively, both p<0.05, after correction for multiple comparisons), but not for polyclonal stimulated cultures (FIG. 2A). A similar trend was seen in CD14+ cells (but not CD19+ cells) although this difference did not survive correction for multiple comparisons (FIG. 2B). After alemtuzumab, caspase 3 expression was significantly increased in T cells and monocytes, reaching levels seen in healthy controls (p<0.05; FIGS. 2A and 2B). Expression of all other genes tested (listed in methods) was unchanged after alemtuzumab.

Thus, our studies show that T cells from people with untreated multiple sclerosis are resistant to apoptosis, and this resistance is associated with under-expression of caspase 3. Consistent with the position of this effector caspase at the convergence point of the extrinsic and intrinsic apoptotic pathways, we have demonstrated T cell resistance both to Fas-mediated and passive apoptosis in our patients. Under-expression of caspase 3 has been described in some autoimmune diseases, including Type I diabetes (Vendrame et al., *Eur J Endocrinol* 152, 119-125 (2005)), Hashimoto's thyroiditis and autoimmune polyendocrine syndrome-2 (Vendrame et al., *J Clin Endocrinol Metabjc* (2006)). This is, however, a novel finding in multiple sclerosis.

Figure 3:
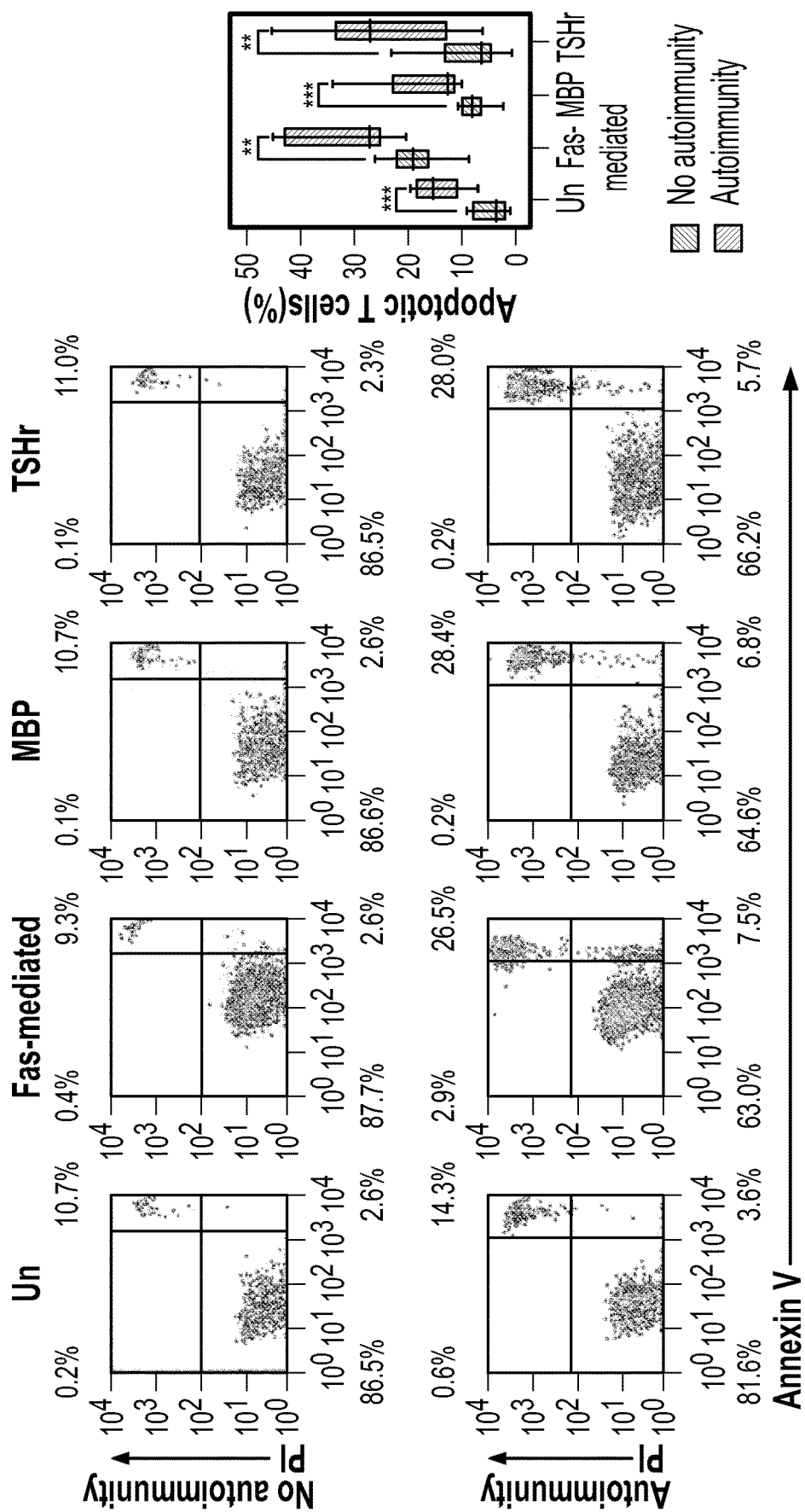
FIG. 3 is plots and a graph showing that autoimmunity after alemtuzumab is associated with excessive T cell apoptosis. Percentage T cell apoptosis that is passive (Un), Fas-mediated, or in response to MBP or TSHr stimulation in those without autoimmunity (Ge et al., *Proceedings of the National Academy of Sciences of the United States of America* 101, 3041-3046 (2004)) or those with secondary autoimmunity (Ge et al., 2004) is shown in separate plots . (* p<0.05,  p<0.01, * p<0.001)

Example 5: Secondary Autoimmunity after Alemtuzumab is Associated with Excessive T Cell Apoptosis Having demonstrated increased lymphocyte proliferation and apoptosis as a generic response to treatment, we tested the relationship between T cell apoptosis and development of autoimmunity after alemtuzumab, defined as development of a novel autoimmune disease and/or persistent autoantibodies above the normal range, after alemtuzumab, sustained over at least 3 months. Using this definition, T cells derived from patients with autoimmunity (n=10) showed significantly higher levels of apoptotic cell death in all culture conditions at 9 months post-treatment, when compared to T cells from non-autoimmune patients (n=10) studied at the same time point (unstimulated 4.7% vs. 14.4%, Fas-mediated 18.2% vs. 32.1%, MBP 7.6% vs. 17.6%, and TSHr 9.5% vs. 25.5%, p<0.01 for all comparisons; FIG. 3). If a stricter definition of autoimmunity was applied, that being development of an autoimmune disease, excluding nonpathogenic antibody production, the difference remained, despite reducing the number in the autoimmune group to 7 (unstimulated, 4.7% vs. 15.4%; Fas mediated, 18.2% vs. 31.7%; MBP, 7.6% vs. 20.2%; TSHr, 9.5% vs. 13.4%; P<0.02 for all comparisons).

There was no difference in the rate of T cell reconstitution between the two groups (e.g., at 6 months, CD4 counts are $0.15 \times 10^9$/L vs. $0.19 \times 10^9$/L; and CD8 counts $0.11 \times 10^9$/L vs. $0.11 \times 10^9$/L in those with and without autoimmunity, respectively), suggesting increased T cell cycling in the autoimmune group (data not shown).

Example 6: IL-21 Induces T Cell Proliferation and Apoptosis

A. IL-21 Assays and Spiking

Serum IL-21 was measured using the EBIOSCIENCE kit (88-7216-86) as per instructions. Plates were read using a microplate reader (model 680, BioRad) at 450 nm. Unstimulated and polyclonally stimulated (1 µg/mL plate-bound anti-CD3 and 1 µg/mL soluble anti-CD28) PBMCs were spiked with 5 pg/mL and 20 pg/mL rhIL-21 (EBIOSCIENCE 14-8219). CD4+ and CD8+ apoptosis and proliferation were assessed as described above.

B. Results

Figure 4A:
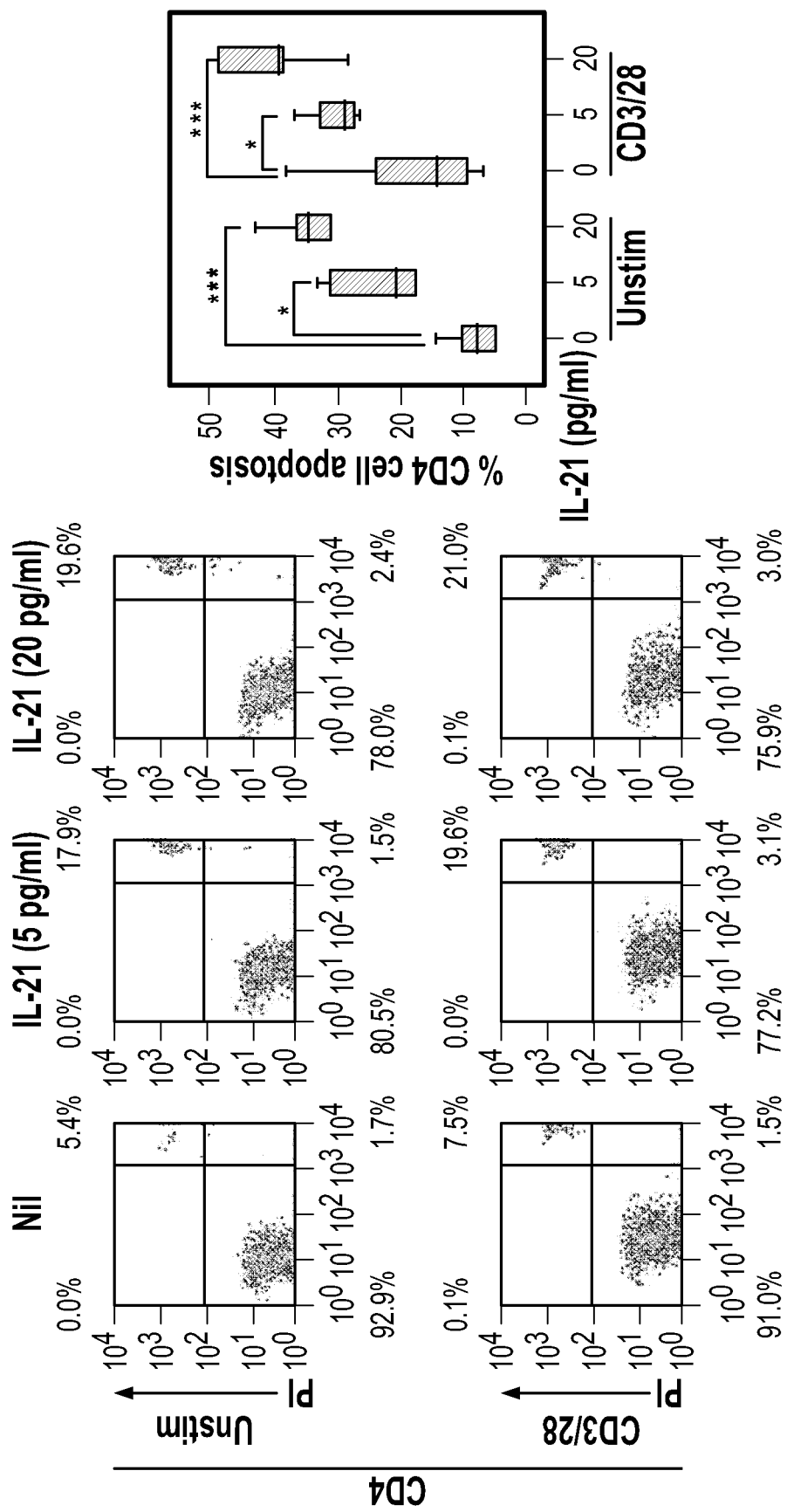
FIGS. 4A and 4B are plots and graphs showing that rhIL-21 induces T cell apoptosis in vitro. They show that (A) CD4+ T cells and (B) CD8+ T cells, respectively, unstimulated or polyclonally stimulated (anti-CD3/CD28), apoptose in response to rhIL-21 in a dose-dependent manner. (* p<0.05,  p<0.01, * p<0.001)
Figure 4B:
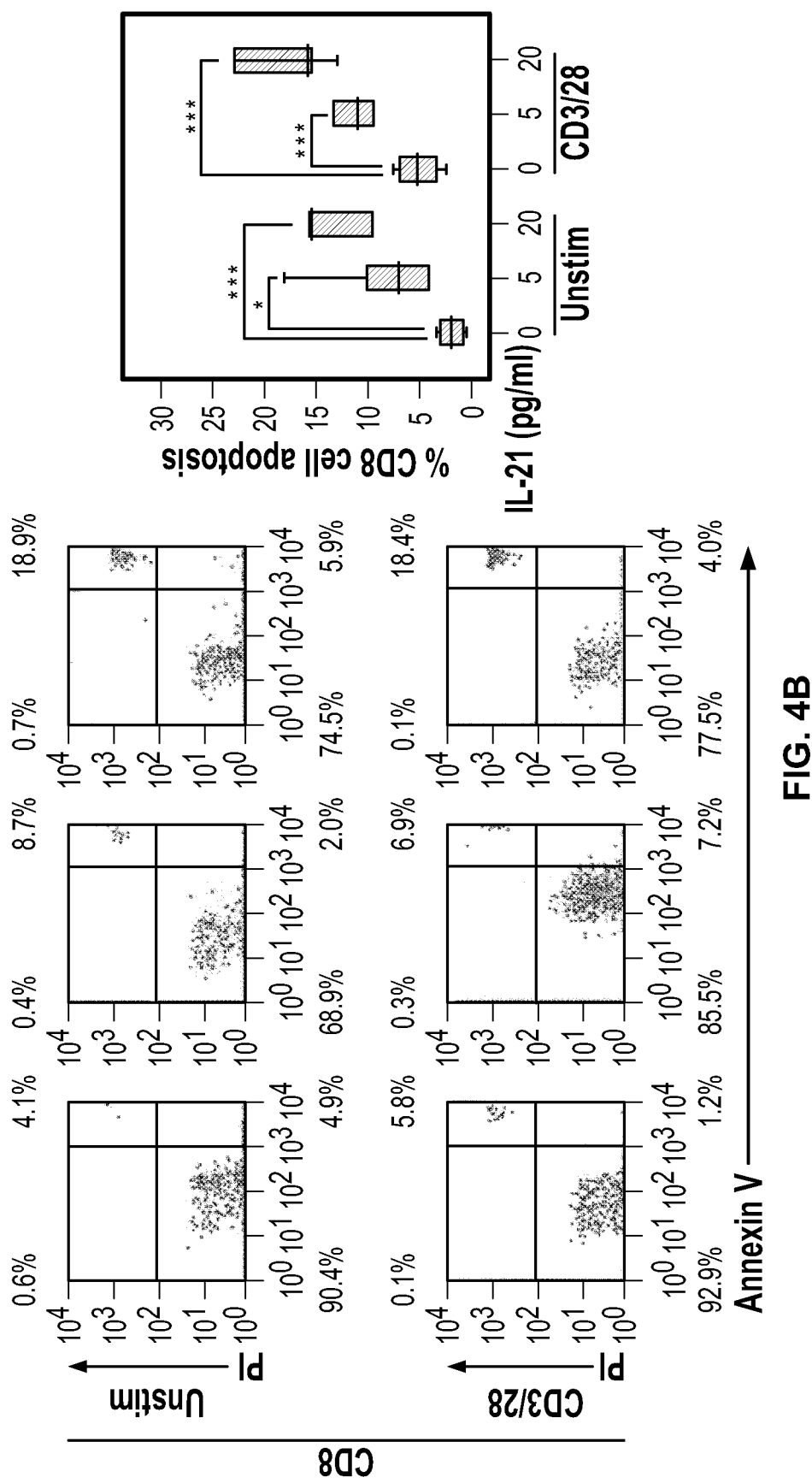
Figure 5A:
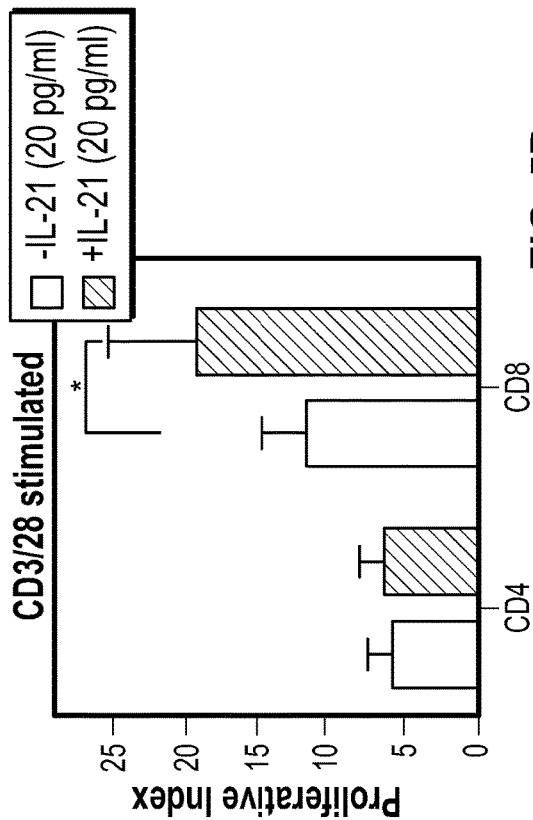
FIGS. 5A-5D are graphs showing that rhIL-21 induces T cell proliferation in vitro.
Figure 5B:
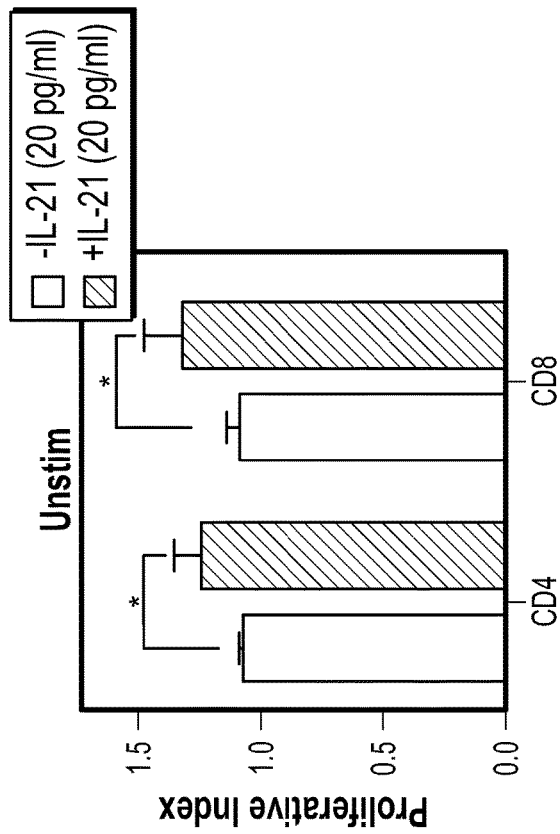
Figure 5D:
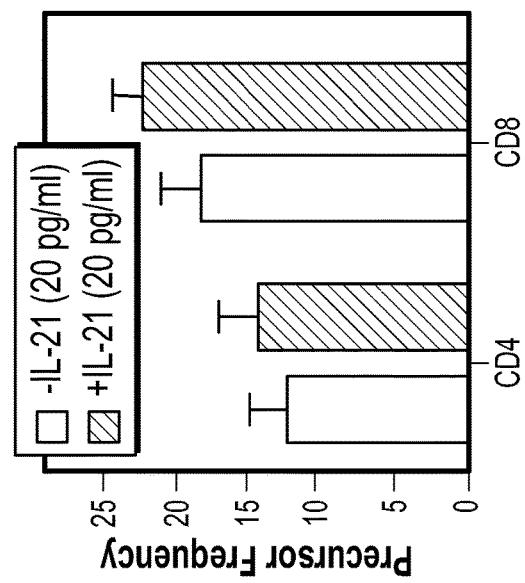
Figure 5C:
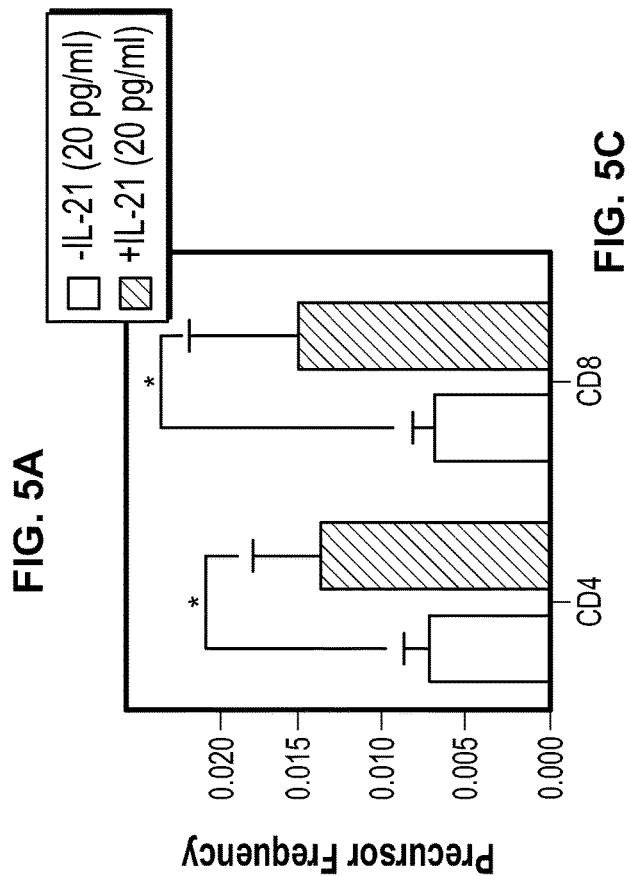
Figure 5E:
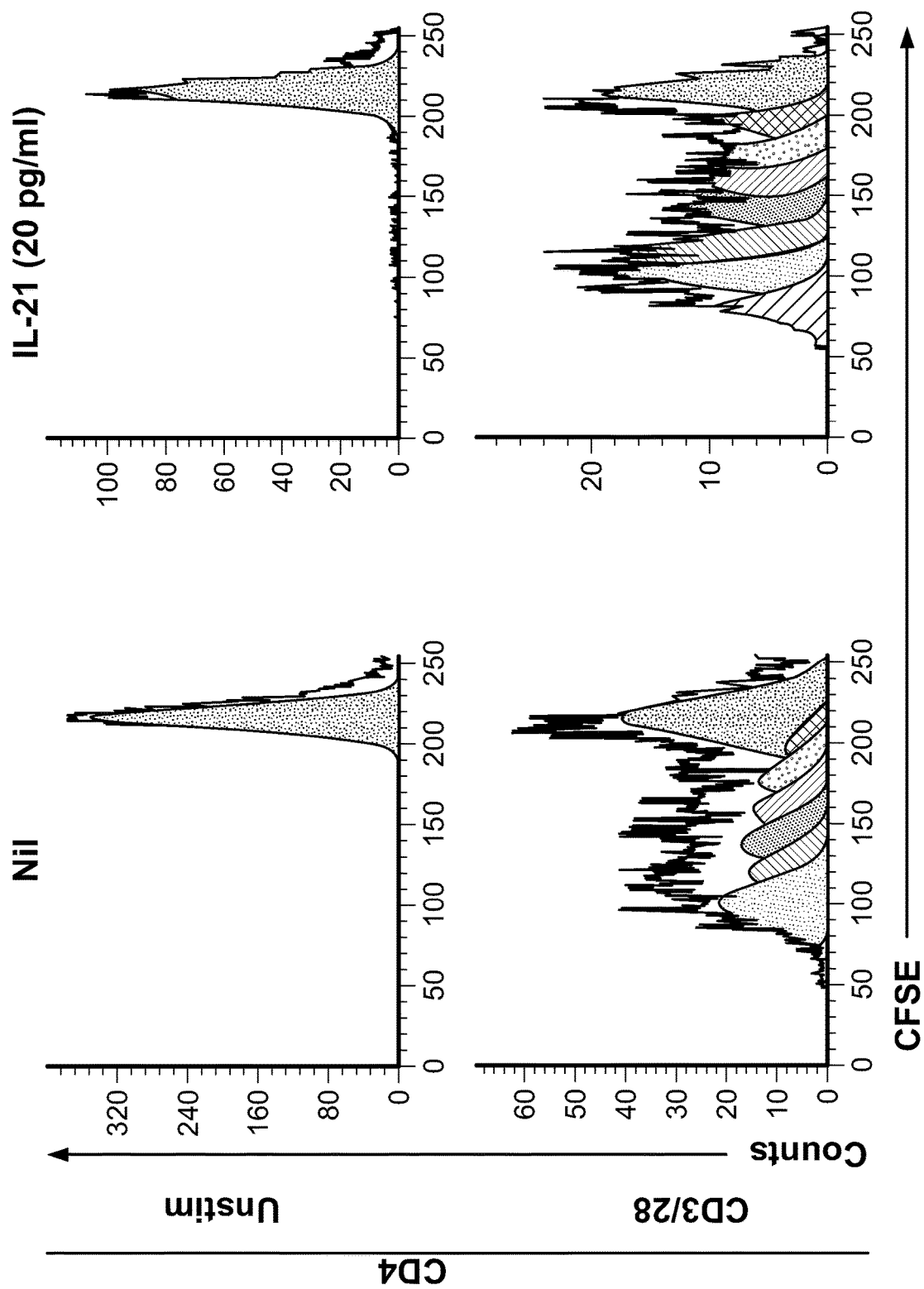
FIG. 5E is plots showing the number of unstimulated or polyclonally stimulated (anti-CD3/CD28) CD4+ or CD8+ cells in different channels in the absence of, or in response to, rhIL-21.
Figure 5E:
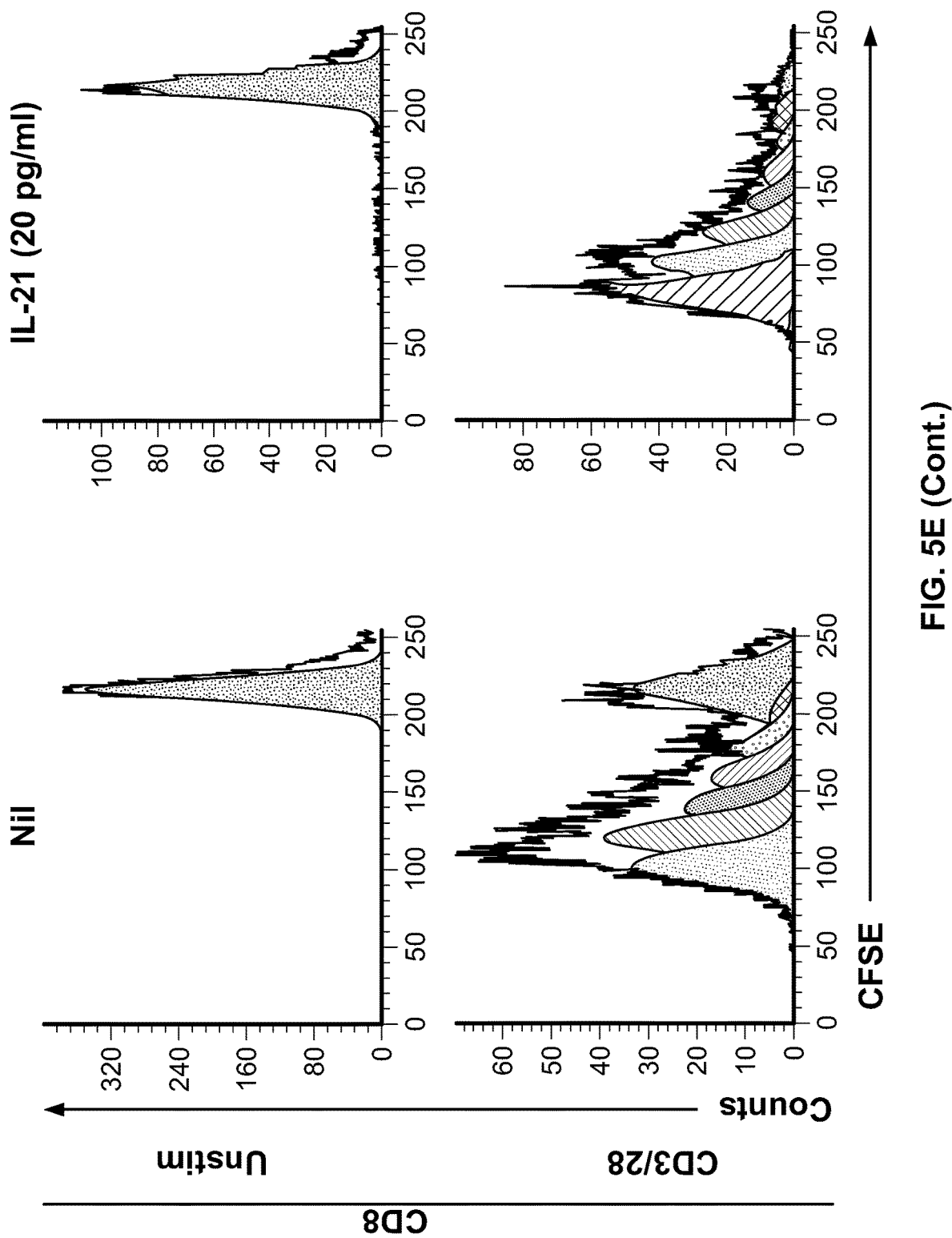

We tested the effect of exogenous IL-21 on apoptosis and proliferation of human T cells in vitro. Spiking PBMCs from healthy controls with rhIL-21 led to an increase in the apoptotic death of unstimulated and polyclonally stimulated CD4+ (FIG. 4A) and CD8+ (FIG. 4B) T cells in a dose dependent manner (p<0.05 for all conditions). Spiking unstimulated cells with rhIL-21 led to a small but significant increase in the proliferation of both CD4+ and CD8+ T cells; with an increase both in proliferative index (CD4+ and CD8+: 1.07 vs. 1.25, p=0.017; and 1.09 vs. 1.32, p=0.017 respectively; FIG. 5A) and precursor frequency (CD4+ 0.007 vs. 0.014, p=0.016; CD8+ 0.007 vs. 0.015, p=0.026; FIG. 5C). IL-21 did not affect the proportion of CD4+ or CD8+ T cells proliferating in response to polyclonal stimulation (FIG. 5D), suggesting that they were already maximally stimulated. IL-21, however, did lead to a significant increase in the extent of CD8+ cell proliferation (proliferative index 11.59 vs. 19.39, p=0.012; FIG. 5B).

Example 7: IL-21 Predicts the Development of Secondary Autoimmunity after Alemtuzumab At all time points in Example 6, the concentration of serum IL-21 was significantly greater in patients who developed secondary autoimmunity compared to the non-autoimmune group (for all comparisons p<0.05; FIG. 6A). We examined all pre-treatment serum samples from 84 patients who subsequently went on to have alemtuzumab. After at least two years of follow up with these patients, we categorized them as being in the "autoimmune" group (n=35:32 patients with thyroid diseases, one ITP, one Goodpasture's, and one Alopecia) or "non-autoimmune" group (n=49: patients with no or only transient (unsustained over six months) autoantibodies)). These pre-treatment sera had a statistically greater mean concentration of IL-21 than controls; however, this was entirely accounted for by high IL-21 levels in those patients who went on to develop secondary autoimmunity. There was a highly significant difference in mean pre-treatment IL-21 levels between those that went on to develop autoimmunity (464 pg/ml) and those that did not (229 pg/ml; p=0.0002) (FIG. 6B).

The association between induced-lymphopenia and autoimmunity has been observed in animal models. Under lymphopenic conditions, the remaining T cells undergo extensive compensatory expansion in order to reconstitute the immune system. This process, termed homeostatic proliferation, relies on stimulation through the TCR-self-peptide-MHC complex (Ge et al., *P.N.A.S.* 101, 3041-3046 (2004); Ge et al., *P.N.A.S.* 98, 1728-1733 (2001); Kassiotis et al., *J Exp. Med.* 197, 1007-1016 (2003)) and results in a population skewed towards increased recognition of self-antigen, as seen in our studies. In addition, rapidly expanding T cells acquire the phenotype and functional characteristics of memory cells including: reduced dependence on co-stimulation, the ability to respond to lower doses of antigen than naïve cells, and the rapid secretion of inflammatory cytokines on restimulation, so further promoting the breakdown of self tolerance (Cho et al., *JExp. Med.* 192, 549-556 (2000); Goldrath et al. *JExp. Med.* 192, 557-564 (2000); Murali-Krishna et al., *J Immunol* 165, 1733-1737 (2000); Wu et al., *Nat Med.* 10, 87-92 (2004)). Yet, despite these changes, autoimmunity is not an inevitable consequence of lymphopenia. Indeed, as with our patients, most lymphopenic subjects did not develop autoimmunity, suggesting that additional "co-factors" are required.

We have demonstrated here for the first time in man that overproduction of IL-21 is the "second hit" required in the development of secondary autoimmunity following otherwise successful treatment of multiple sclerosis with a lymphocyte depleting agent such as alemtuzumab. Our studies show that autoimmunity arises in lymphocyte-depleted patients, with greater T cell apoptosis and cell cycling driven by genetically influenced higher levels of IL-21 that are detectable even before treatment. Even before treatment, patients who went on to develop secondary autoimmunity had more than 2-fold greater levels of serum IL-21 than the nonautoimmune group, suggesting that serum IL-21 may serve as a biomarker for the risk of developing autoimmunity months to years after alemtuzumab treatment. Without wishing to be bound by any theory, we believe that, by driving cycles of T cell expansion and death to excess, IL-21 increases the probability of generating self-reactive T cells, and hence, for autoimmunity. Thus, cytokine-induced abnormal T cell cycling is a general principle of lymphopenia-associated autoimmunity.

Example 8: IL-21 Genotype Influences IL-21 Expression and Associates with Autoimmunity A. IL-21 Genotyping In total, four SNPs, rs13151961, rs6822844, rs4833837 and rs6840978, which lie in a region of strong linkage disequilibrium containing four genes, KIAA1109-ADAD1-IL2-IL21, on chromosome 4q27 were tested. All four SNPs were available as Applied Biosystems Assay-On-Demand (AoD) products. SNP genotyping was performed using Applied Biosystems TaqMan methodology according to the manufacturer's recommended conditions. Polymerase chain reaction (PCR) was performed on Applied Biosystems 384-well 9700 Viper PCR machines, after which genotypes were called on a 7900 High Throughput Sequence Detection System (SDS) using SDS Software Version 2.1. Each individual was genotyped in duplicate. All individuals were additionally genotyped for the multiple sclerosis associated genetic factors: HLA-DRB1*1501, rs2104286 (IL2RA) and rs6897932 (IL7R).

B. Results

In order to determine whether there is an association between genetic variation and IL-21 production, we genotyped 73 subjects, in whom pre-alemtuzumab serum IL-21 concentration had been determined, for four single nucleotide polymorphisms (SNPs) that lie within a block of linkage disequilibrium (LD) on chromosome 4q27 encoding the IL-21 gene. The minor allele frequency for all four SNPs was in line with published data: rs13151961G (14.5%), rs6822844T (14.6%), rs4833837G (38.0%) and rs6840978T (18.1%) (Glas et al., *Am. J. Gastroenterol.* 104, 1737-1744 (2009)). We found that the genotype at 3 of the 4 SNPs (rs13151961 A/A, rs6822844 G/G and rs6840978 C/C) was associated with significantly higher levels of serum IL-21 (p values: 0.0076, 0.0098 and 0.0067 respectively). The genotype at rs4833837 did not influence IL-21 production. The LD between rs4833837 and the three other SNPs is low ($r^2$<0.15), therefore a SNP which lies on the haplotype rs13151961(A)-rs6822844(G)-rs6840978(C) is most likely to be associated with increased IL-21 production. The genotype frequencies for HLA-DRB1*1501, rs2104286 (IL2RA) and rs6897932 (IL7R) did not differ from published data for other unselected patients with multiple sclerosis (International Multiple Sclerosis Genetics Consortium (IMSGC), *Lancet Neurol.* 7, 567-569 (2008); Yeo et al., *Ann Neurol* 61, 228-236 (2007)).

Finally, in order to address whether genotype influences susceptibility to autoimmunity after alemtuzumab, we categorized as many patients as possible into those who did (27 subjects) and definitely did not (23 subjects) develop autoimmunity post-alemtuzumab. 23 patients could not be categorized due to transient autoantibody production and/or insufficient time since exposure to alemtuzumab. The genotypes (rs13151961 A/A, rs6822844 G/G, rs6840978 C/C), shown to be associated with higher serum IL-21 concentration, were also found to be associated with autoimmunity after alemtuzumab.

What is claimed is:

1. A method for treating a multiple sclerosis (MS) patient, comprising the steps of:
    identifying an MS patient who has been diagnosed as being in need of heightened monitoring for development of a secondary autoimmune disease after lymphocyte depleting therapy, wherein the need has been diagnosed by measuring IL-21 in a blood sample from the patient, wherein elevated IL-21 in said patient compared to a subject without an autoimmune disease indicates that the patient is in need of heightened monitoring for development of a secondary autoimmune disease after lymphocyte depleting therapy, compared to MS patients without elevated IL-21;
    administering alemtuzumab to said patient; and
    monitoring said patient for development of a secondary autoimmune disease.

2. The method of claim 1, further comprising administering an IL-21 antagonist to the patient.

3. A method for treating a multiple sclerosis (MS) patient, comprising the steps of:
    identifying an MS patient who has been diagnosed as not being at increased risk of developing a secondary autoimmune disease after lymphocyte depleting therapy, wherein the risk has been diagnosed by measuring IL-21 in a blood sample from the patient, wherein a normal IL-21 level compared to a subject without an autoimmune disease indicates that the patient is not at increased risk of developing a secondary autoimmune disease after lymphocyte depleting therapy, compared to MS patients without elevated IL-21; and
    administering alemtuzumab to said patient.

4. The method of claim 1, wherein the IL-21 measured is serum IL-21.

5. The method of claim 1, wherein the secondary autoimmune disease is selected from the group consisting of: immune thrombocytopenic purpura (ITP), Graves' disease, Goodpasture's disease, autoimmune thyroid disease, autoimmune hemolytic anemia, autoimmune neutropenia, and autoimmune lymphopenia.

6. The method of claim 1, wherein the blood sample is obtained from the patient prior to a lymphocyte depleting therapy.

7. The method of claim 1, wherein the multiple sclerosis is relapsing-remitting multiple sclerosis, primary progressive multiple sclerosis, or secondary progressive multiple sclerosis.

8. The method of claim 3, wherein the IL-21 measured is serum IL-21.

9. The method of claim 3, wherein the secondary autoimmune disease is selected from the group consisting of: immune thrombocytopenic purpura (ITP), Graves' disease, Goodpasture's disease, autoimmune thyroid disease, autoimmune hemolytic anemia, autoimmune neutropenia, and autoimmune lymphopenia.

10. The method of claim 3, wherein the blood sample is obtained from the patient prior to a lymphocyte depleting therapy.

11. The method of claim 3, wherein the multiple sclerosis is relapsing-remitting multiple sclerosis, primary progressive multiple sclerosis, or secondary progressive multiple sclerosis.

* * * * *